US009403875B2

(12) United States Patent
Conti et al.

(10) Patent No.: US 9,403,875 B2
(45) Date of Patent: Aug. 2, 2016

(54) CAGE-LIKE BIFUNCTIONAL CHELATORS, COPPER-64 RADIOPHARMACEUTICALS AND PET IMAGING USING THE SAME

(75) Inventors: Peter S. Conti, Pasadena, CA (US); Hancheng Cai, Alhambra, CA (US); Zibo Li, Logan, UT (US); Shuanglong Liu, Alhambra, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 348 days.

(21) Appl. No.: 12/695,125

(22) Filed: Jan. 27, 2010

(65) Prior Publication Data
US 2010/0196271 A1 Aug. 5, 2010

Related U.S. Application Data

(60) Provisional application No. 61/147,709, filed on Jan. 27, 2009.

(51) Int. Cl.
| | |
|---|---|
| *A61K 51/00* | (2006.01) |
| *A61M 36/14* | (2006.01) |
| *C07K 7/08* | (2006.01) |
| *A61K 51/04* | (2006.01) |
| *A61K 51/08* | (2006.01) |
| *C07D 487/08* | (2006.01) |
| *C07K 5/113* | (2006.01) |

(52) U.S. Cl.
CPC ............ *C07K 7/086* (2013.01); *A61K 51/0482* (2013.01); *A61K 51/082* (2013.01); *A61K 51/088* (2013.01); *C07D 487/08* (2013.01); *C07K 5/1021* (2013.01)

(58) Field of Classification Search
CPC ........... A61K 2123/00; A61K 2121/00; A61K 38/00; A61K 38/03; A61K 38/04; A61K 38/06; A61K 38/12; A61K 38/41; A61K 38/07; A61K 41/0057; A61K 41/0038; A61K 41/0071; A61K 41/0076; A61K 51/088; A61K 51/08; A61K 51/00; A61K 51/02; A61K 51/04; A61K 51/041; A61K 51/044; A61K 51/0485; A61K 51/0497; A61K 51/06; A61K 51/065; A61K 51/082; A61K 49/06; A61K 49/08; A61K 49/001; A61K 49/0017; A61K 49/0036; A61K 49/0045; A61K 49/005; A61K 49/0056; A61K 49/085; A61K 49/10; A61K 49/00; A61K 49/0002; C07D 487/22; C07D 487/08; C07D 259/00; C07F 9/00; C07K 5/1021; C07K 7/086
USPC ........... 424/1.11, 1.49, 1.65, 1.69, 1.73, 1.81, 424/9.1, 9.3, 9.36, 9.361, 9.362, 9.363; 514/1, 1.11; 534/7, 10–16; 530/300, 530/316, 317, 330, 331
See application file for complete search history.

(56) References Cited

U.S. PATENT DOCUMENTS

| | | | | |
|---|---|---|---|---|
| 5,053,493 A | * | 10/1991 | Pak et al. | ............ 530/391.5 |
| 5,175,343 A | * | 12/1992 | Fritzberg et al. | ............ 560/145 |
| 5,242,679 A | * | 9/1993 | Fritzberg et al. | ............ 424/1.53 |

OTHER PUBLICATIONS

Cai et al (Dalton Trans., 2009, pp. 5395-5400).*
Di Bartolo et al, J. Chem. Soc., Dalton Trans., 2001, pp. 2303-2309.*
Donnelly et al (J. Chem. Soc., Dalton Trans., 2002, pp. 906-913).*
Katsunori Tanaka, et al., PET (positron emission tomography) imaging of biomolecules using metal-DOTA complexes: a new collaborative challenge by chemists, biologists, and physicians for future diagnostics and exploration of in vivo dynamics†, Organic Biomolecular Chemistry (2008), vol. 6, pp. 815-828.
Shuang Liu, "Radiolabeled Multimeric Cyclic RGD Peptides as Integrin $α_vβ_3$ Targeted Radiotracers for Tumor Imaging", Molecular Pharmaceutics vol. 3, No. 5, pp. 472-487.
Gilles Gasser, et al., "Synthesis, Copper (II) Complexation, $^{64}$Cu-Labeling, and Bioconjugation of a New Bis(2-pyridylmethyl) Derivative of 1,4,7-Triazacyclononane", Bioconjugate Chem. (2008), vol. 19, No. 3, pp. 719-730.
Xiaoyuan Chen, et al., "MicroPET and Autoradiographic Imaging of Breast Cancer $α_v$-Integrin Expression Using $^{18}$F- and $^{64}$Cu-Labeled RGD Peptide", Bioconjugate Chem. (2004), vol. 15, No. 1, pp. 41-49.
Adam F. Prasanphanich, et al., "In vitro and in vivo analysis of [$^{64}$Cu-NO2A-8-Aoc-BBN(7-14)NH$_2$]: a site-directed radiopharmaceutical for positron-emission tomography imaging of T-47D human breast cancer tumors", Nuclear Medicine and Biology, (2009), vol. 36, pp. 171-181.
Lihui Wei, et al., "$^{64}$Cu-Labeled CB-TE2A and diamsar-conjugated RGD peptide analogs for targeting angiogenesis: comparison of their biological activity", Nuclear Medicine and Biology (2009) vol. 36, pp. 277-285.

* cited by examiner

*Primary Examiner* — D L Jones
(74) *Attorney, Agent, or Firm* — DLA Piper LLP (US)

(57) ABSTRACT

Disclosed is a class of versatile Sarcophagine based bifunctional chelators (BFCs) containing a hexa-aza cage for labeling with metals having either imaging, therapeutic or contrast applications radiolabeling and one or more linkers (A) and (B). The compounds have the general formula

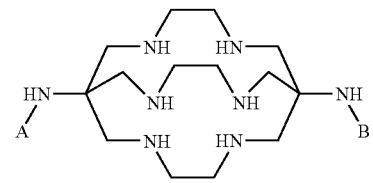

where A is a functional group selected from group consisting of an amine, a carboxylic acid, an ester, a carbonyl, a thiol, an azide and an alkene, and B is a functional group selected from the group consisting of hydrogen, an amine, a carboxylic acid, and ester, a carbonyl, a thiol, an azide and an alkene. Also disclosed are conjugate of the BFC and a targeting moiety, which may be a peptide or antibody. Also disclosed are metal complexes of the BFC/targeting moiety conjugates that are useful as radiopharmaceuticals, imaging agents or contrast agents.

5 Claims, 23 Drawing Sheets

Scheme 1

Scheme 1

CAGE-LIKE BIFUNCTIONAL CHELATORS, COPPER-64 RADIOPHARMACEUTICALS AND PET IMAGING USING THE SAME

CROSS-REFERENCE TO RELATED APPLICATIONS

This application claims the benefit of U.S. Provisional Application No. 61/147,709 filed Jan. 27, 2009, the entire contents of which are incorporated by reference.

STATEMENT REGARDING FEDERALLY SPONSORED RESEARCH AND DEVELOPMENT

This work was supported by research grant from the Department of Energy. The government has certain rights in the invention.

BACKGROUND OF THE INVENTION

Molecular imaging is an emerging technology that allows for visualization of interactions between molecular probes and biological targets. Positron emission tomography (PET), micro-PET and PET/CT, are state-of-the-art nuclear medicine imaging modalities, which use nano- to picomolar concentrations of the corresponding probes (radiotracers) to achieve images of biological processes within the living system. Selection of the proper radionuclide and synthetic approach for radiotracer design are critical. Positron-emitting isotopes frequently used include $^{11}$C and $^{18}$F. One non-traditional PET radionuclide, $^{64}$Cu, shows promise as both a suitable PET imaging and therapeutic radionuclide due to its nuclear characteristics ($T_{1/2}$=12.7 h, $\beta^+$: 17.4%, $E_{\beta+max}$=656 keV; $\beta^-$: 39%, $E_{\beta-max}$=573 keV), and the availability of its large-scale production with high specific activity.

Stable attachment of radioactive $^{64}$Cu$^{2+}$ to targeted imaging probes requires the use of a bifunctional chelator (BFC), which is used to connect a radionuclide and bioactive molecule to form the $^{64}$Cu-radiopharmaceutical. Extensive efforts have been devoted to the development of BFCs for $^{64}$Cu labeling. Three of the most common chelators studied have been the macrocyclic ligands DOTA (1,4,7,10-tetraazacyclododecane-N,N',N'',N'''-tetraacetic acid), TETA (1,4,8,11-tetraazacyclotetradecane-N,N',N'',N'''-tetraacetic acid), and cross-bridged tetraamine ligands. (Refs. 1-3) However, dissociation of $^{64}$Cu from the BFC in vivo and harsh labeling conditions (e.g., incubation at 75° C. under basic conditions) impair the use of these chelators in preparing biomolecule-based $^{64}$Cu-radiopharmaceuticals. (Ref. 4) The BFC DOTA has been used for $^{64}$Cu$^{2+}$ labeling. (Refs. 3, 5, 6) However, the limited stability of the copper chelate in vivo has hindered its application. (Ref. 37)

The integrin $\alpha_v\beta_3$ receptor has been the attractive target of intensive research given its major role in several distinct processes, such as tumor angiogenesis and metastasis, and osteoclast mediated bone resorption. (Refs. 7, 8) The molecular imaging of integrin $\alpha_v\beta_3$ expression will allow the detection of cancer and other angiogenesis related diseases, patient stratification, and treatment monitoring of anti-angiogenesis based therapy. (Refs. 9, 10) Although we and others have successfully developed various DOTA conjugated RGD peptides for multimodality imaging of integrin $\alpha_v\beta_3$ expression. (Refs. 9, 10, 11, 31), the loss of $^{64}$Cu from the chelator has lead to unfavorable high retention in liver, resulting in high background. Therefore, the choice of a more stable BFC is preferred.

Although some other novel BFCs have been developed and shown promise for use in copper-64 labeling (Refs. 2, 4, 12, 32), there is lack of adequate published data regarding the biological activity of these complexes. Some have high uptake in lung, liver and muscle, which may impair the detection of small lesions in the chest or/and abdominal regions. (Refs. 2, 4, 12, 32)

Recently, Sargeson and co-workers reported a new type BFC based on the sarcophagine (3, 6, 10, 13, 16,19-hexaazabicyclo[6.6.6]icosane, Sar, FIG. 1. A-2) for preparation of $^{64}$Cu-radiopharmaceuticals, (Refs. 2, 36) These ligands coordinate $^{64}$Cu$^{2+}$ within the multiple macrocyclic rings comprising the Sar cage structure, yielding stable complexes that are inert to the dissociation of the metal ion.

The caged-like BFC Sar ligands are able to selectively label $^{64}$Cu$^{2+}$ rapidly over a wider range of pH value under mild conditions. (Ref. 2) However, there are only a few reports that describe the complexation, stability and biodistribution of the $^{64}$Cu complexes of the Sar ligand, and only (NH$_2$)$_2$-Sar (Diamsar) and 1-N-(4-aminobenzyl)-3,6,10,13,16,19-hexaazabicyclo[6.6.6]icosane-1,8-diamine (SarAr) have been reported as a BFC for the development of $^{64}$Cu-radiopharmaceuticals. (Refs. 2, 13, 35, 36) Moreover, the relatively nontrivial and multi-step synthesis of Sar ligands may limit their future applications. (Ref. 4) However, the SARAR BFC utilizes the C-terminal for carboxylic acid for conjugation. This may be a disadvantage as the C-terminus is often found to be a crucial part for maintaining biological activity.

As such, there is a need for improved bifunctional chelators that can efficiently form stable complexes with metals, including Copper-64 under mild conditions.

There is also a need for new radiopharmaceuticals and imaging agents that are stable in vivo for imaging and other.

There is also a need for simplified methods for making bifunctional chelators.

BRIEF SUMMARY OF THE INVENTION

It is one object of the present invention to provide improved bifunctional chelators (BFCs) that form stable complexes with metals, including Copper-64, that are stable in vivo.

It is another object of the present invention to provide BFC/Targeting Moiety conjugates that specifically target biomolecules.

It is another object of the present invention to provide BFC/Targeting Moiety conjugate complexed with metals useful as imaging, therapeutic or contrast agents.

One embodiment of the present invention is directed to bifunctional chelators having the general formula

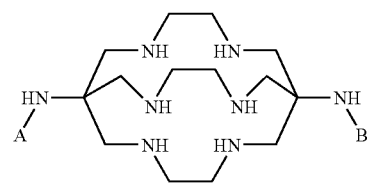

where A is a functional group selected from group consisting of an amine, a carboxylic acid, an ester, a carbonyl, a thiol, an azide and an alkene, and B is a functional group selected from the group consisting of hydrogen, an amine, a carboxylic acid, and ester, a carbonyl, a thiol, an azide and an alkene. In one preferred embodiment, A is a carboxylic acid, or a salt or ester thereof. Even more preferably, A is a carboxylic acid having the formula

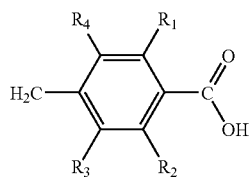

and wherein $R_1$, $R_2$, $R_3$, and $R_4$ are independently selected from the group consisting of H, halogen, alkyl, alkoxy or alkene, or a salt or ester thereof. In a preferred embodiment, $R_1$, $R_2$, $R_3$, and $R_4$ are hydrogen.

In another preferred embodiment, the bifunctional chelators are

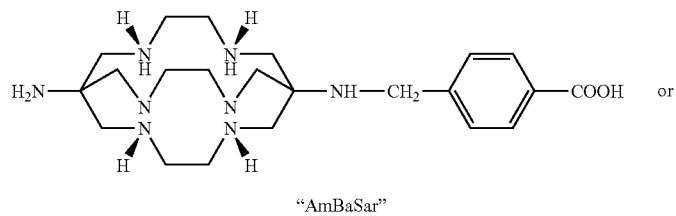

"AmBaSar"

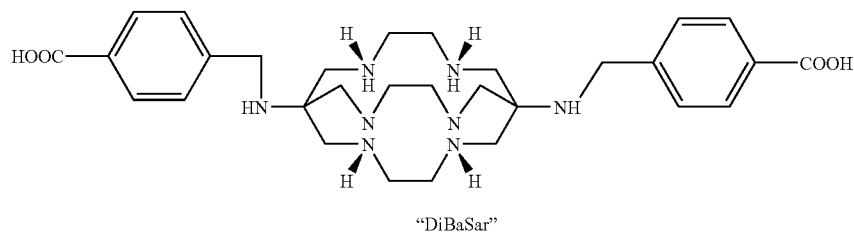

"DiBaSar"

or a salt or ester thereof.

Another embodiment of the present invention is directed to bifunctional chelator/Targeting Moiety conjugates in which a bifunctional chelator is conjugated to a targeting moiety. In the conjugate, the bifunctional chelator is

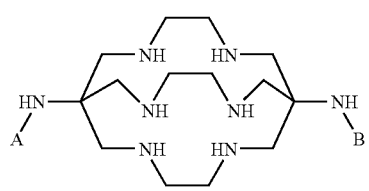

where A is a functional group selected from group consisting of an amine, a carboxylic acid, an ester, a carbonyl, a thiol, an azide and an alkene, and B is a functional group selected from the group consisting of hydrogen, an amine, a carboxylic acid, and ester, a carbonyl, a thiol, an azide and an alkene, or a salt or ester thereof. In a preferred embodiment, the targeting moiety is selected from the group consisting of a peptide and antibody. For instance, the targeting moiety may be a peptide selected from the group consisting of a RGD, Asp-Gly-Glu-Ala (DGEA) (SEQ. ID NO: 1), bombesin peptides (BBN), uPAR peptides, and other peptides with a lysine amine or N-terminal.

Another embodiment of the present invention is directed to a kit having a bifunctional chelator/Targeting Moiety conjugate with instructions for complexing a metal to the bifunctional chelator/Targeting Moiety conjugate.

The present invention is also directed new compositions comprising a bifunctional chelator conjugated to a Targeting moiety and complexed with a metal. These new compositions are useful as radiopharmaceuticals, therapeutic agents or contrast agents. In these compositions, the bifunctional chelator is

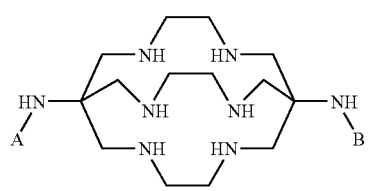

where A is a functional group selected from group consisting of an amine, a carboxylic acid, an ester, a carbonyl, a thiol, an azide and an alkene, and B is a functional group selected from the group consisting of hydrogen, an amine, a carboxylic acid, and ester, a carbonyl, a thiol, an azide and an alkene, or a salt or ester thereof. In these complexes, metal resides within the Sar cage and is bonded to one or more nitrogen. Preferably, the metal may be of $^{90}$Y, Gd, $^{68}$Ga, $^{57}$Co, $^{60}$Co, $^{52}$Fe, $^{64}$Cu or $^{67}$Cu.

In one preferred embodiment, the present application is directed to a radiopharmaceutical comprising $^{64}$Cu-AmBaSar-RGD, either alone or together with a carrier.

DETAILED DESCRIPTION OF THE INVENTION

One embodiment of the present invention is directed to a class of versatile Sarcophagine based bifunctional chelators containing a hexa-aza cage for labeling with metals having either imaging, therapeutic or contrast applications radiolabeling and one or more linkers (A) and (B). The compounds of the present invention have the general formula

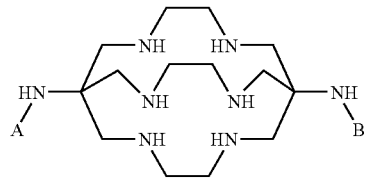

where A is a functional group selected from group consisting of an amine, a carboxylic acid, an ester, a carbonyl, a thiol, an azide and an alkene, and B is a functional group selected from the group consisting of hydrogen, an amine, a carboxylic acid, and ester, a carbonyl, a thiol, an azide and an alkene. Suitable linker group A and B should be of sufficient length (~6 atom lengths) and should incorporate a reactive group that can be readily attached to a range of target agents, but not interfere with efficient and selective complexation of a metal ion like $Cu^{2+}$ to the sarcophagine cage, as well as the target agent's biological activity. (Ref. 16)

In one embodiment of the present invention, linkers A or B, or both, may preferably be a carboxylic acid of the following formula:

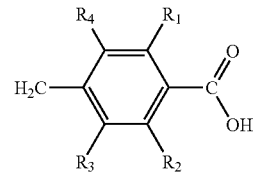

Where $R_1$, $R_2$, $R_3$, and $R_4$ are independently selected from the group consisting of H, halogen, alkyl, alkoxy or alkene.

In another embodiment of the present invention, the bifunctional chelators are sarcophagine based compositions, referred to herein as AmBaSar and DiBaSar, having the having the following structure:

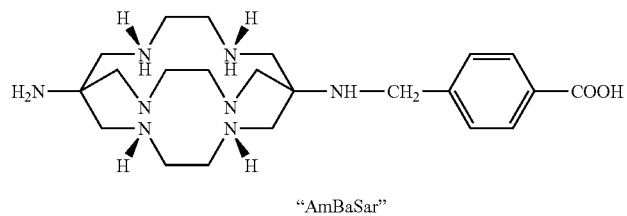

"AmBaSar"

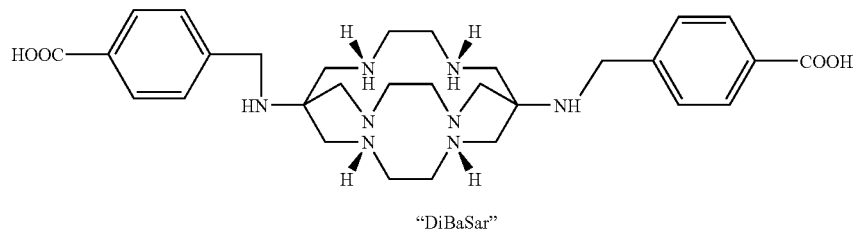

"DiBaSar"

The bifunctional chelators may be conjugated to a targeting moiety as BFC/Targeting Moiety conjugates that specifically target a range of biological molecules. In two separate embodiments, the targeting moiety is a peptide or an antibody.

For instance, the pendant carboxylate group of carboxylic acid (ROOH) functionalized BFC, including AmBaSar and DiBaSar, can be directly conjugated to the amine of lysine in biological molecules, which permit the development of new biomolecule-based $^{64}$Cu-radiopharmaceuticals. More specifically, the BFC's can be used to directly conjugate targeting peptides (Z) through the formation of an amide bond with the peptide to form BFC peptide conjugates of the following structure:

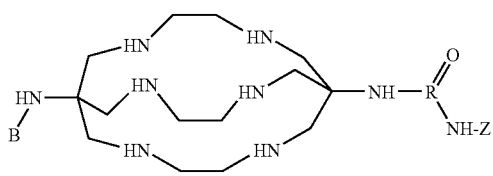

where Z is a targeting peptide containing lysine.

Examples of the peptides to which AmBaSar, and other carboxylic acid based BFCs may be conjugated include, but are not limited to, the small cyclic peptide Arg-Gly-Asp (RGD). Asp-Gly-Glu-Ala (DGEA) (SEQ ID NO: 1), bombesin peptides (BBN), uPAR peptides, and other peptides with a lysine amine or N-terminal. Sar-DGEA is directly conjugated to the Sar cage without functionalization by solid or liquid phase methods well known in the art. In vitro and in vivo evaluation of the AmBaSar-RGD demonstrates the potential of the BFC's of this invention for preparation of a range of radiopharmaceuticals.

Figure 14:
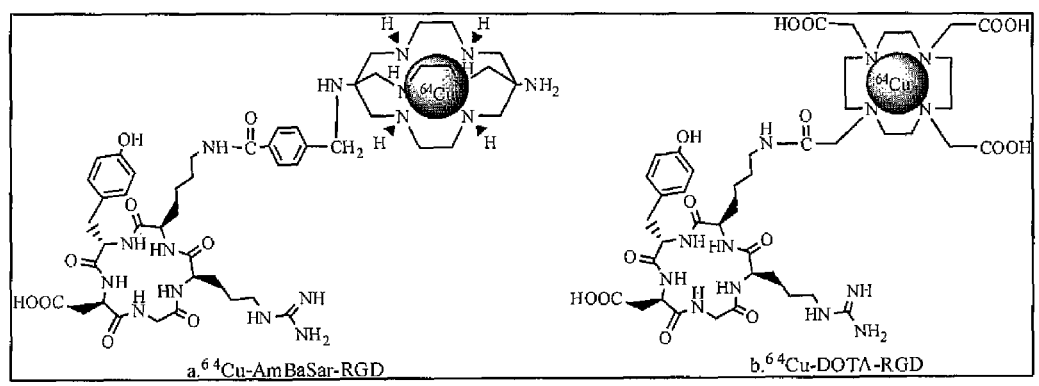
FIG. 14 is a chart comparing the chemical structures of $^{64}$Cu-AmBaSar-RGD and $^{64}$Cu-DOTA-RGD.

The BFC and the BFC/Targeting Moiety conjugates of the present invention may be complexed with a range of metals by known methods to produce radiopharmaceuticals for imaging or therapy. The use of the word "metal" or "metals" throughout this specification should be understood to include metal ions and their salts. The BFC and the BFC/Targeting Moiety conjugates may also be combined with paramagnetic metals for use as contrast agents in MR imaging or with these or other metals for CT scanning applications. Examples of suitable metal ions for use in the present invention include, but are not limited to, $^{90}$Y, Gd, $^{68}$Ga, $^{57/60}$Co, $^{52}$Fe, $^{64/67}$Cu In the Metal-BFC and Metal-BFC/Targeting Moeity complexes of the present invention, the metal resides within the Sar cage bound to the nitrogen of the Sar Cage as shown in FIG. 14 for $^{64}$Cu-AmBaSar-RGD.

In order to form the radiopharmaceuticals in accordance with the present invention, the BFC/Targeting Moiety conjugates complexed with a metal may be dispersed or dissolved in a suitable carrier in appropriate concentrations and delivered to the patient in appropriate doses. Preferred routes of delivery are oral, injection, or infusion. The identity of the carrier is not particularly limited so long as the radiopharmaceutical is stable in the carrier. Suitable carriers for use in connection with the present invention include Saline (0.9%), Phosphate Buffer Solution, or Ethanol solution (<8%). The carrier may optionally include HSA protein, synthetic polymers, dendrimers, cyclodextron et al. The active species should be delivered in an amount effective to produce the desired effect but below the level where there is unacceptable toxicity. When used in solution, concentration of active species in the carrier should be sufficiently high to produce the desired effect but below the level where there is significant toxicity. Typical concentrations for imaging applications are approximately in the range of 1-20 mCi/mL.

In one example of the present invention, AmBaSar is conjugated to the small cyclic Arg-Gly-Asp (RGD) peptide, and subsequently labeled with $^{64}$Cu, to provide a new PET probe $^{64}$Cu-AmBaSar-RGD for imaging the $\alpha_v\beta_3$ integrin receptor. $^{64}$Cu-AmBaSar-RGD has the following formula:

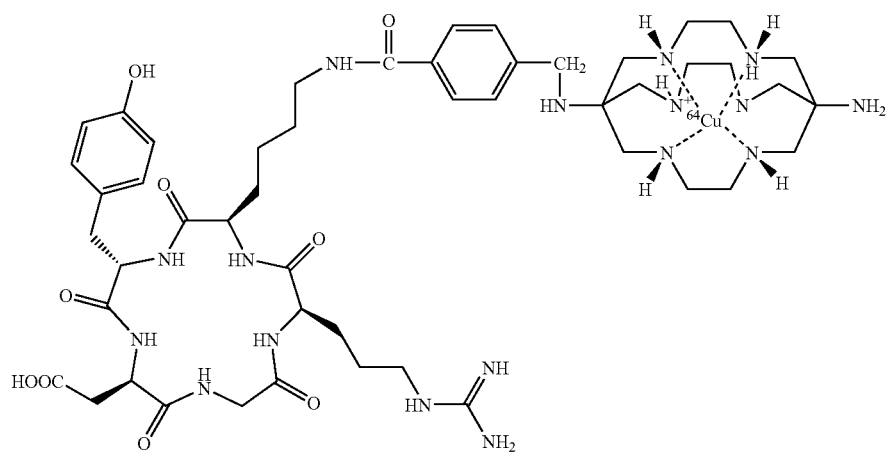

Another embodiment of the present invention is directed to new radiopharmaceuticals comprising $^{64}$Cu-AmBaSar-RGD. $^{64}$Cu-AmBaSar-RGD is obtained with high radiochemical yield (≥95%) and purity (≥99%) under mild conditions (pH 5.0~5.5, 23~37° C.) in less than 30 min. In order to form the radiopharmaceuticals in accordance with the present invention, $^{64}$Cu-AmBaSar-RGD may be dispersed or dissolved in a suitable carrier in appropriate concentrations delivered to the patient in appropriate doses orally, or by injection, infusion or, where possible. Suitable carriers for use in connection with $^{64}$Cu-AmBaSar-RGD include Saline (0.9%), Phosphate Buffer Solution, or Ethanol solution (≤8%). Carrier may include HSA protein, synthetic polymers, dendrimers, cyclodextron et al. The concentration of $^{64}$Cu-AmBaSar-RGD in the carrier should be sufficiently high to produce sufficient signal to permit tracking and/or imaging of the $^{64}$Cu-AmBaSar-RGD within the patient after deliver but below the level where there is significant toxicity. Suitable concentrations for the $^{64}$Cu-AmBaSar-RGD are preferably 1~20 mCi/mL.

In another embodiment of the present invention, a kit comprises a BFC/Targeting Moiety conjugate together with instructions for forming the metal complex with the BFC/Targeting Moiety conjugate.

The BFC, BFC/Targeting Moiety and the BFC/Targeting Moiety conjugate complexed with a metal may each be in the form of a pharmaceutically acceptable salts or ester form. Any carboxylic acid described herein is also understood to encompass pharmaceutically salt or esters of the carboxylic acid.

Metabolic studies support the observation that $^{64}$Cu-AmBaSar-RGD is more stable in vivo than $^{64}$Cu-DOTA-RGD. In vitro and in vivo evaluations of the $^{64}$Cu-AmBaSar-RGD demonstrate its improved stability compared with the established tracer $^{64}$Cu-DOTA-RGD. For in vitro studies, the radiochemical purity of $^{64}$Cu-AmBaSar-RGD was more than 97% in the PBS or FBS and 95% in mouse serum after 24 hr incubation. The log P value of $^{64}$Cu-AmBaSar-RGD was −2.44±0.12. For in vivo studies, $^{64}$Cu-AmBaSar-RGD and $^{64}$Cu-DOTA-RGD have demonstrated comparable tumor uptake at selected time points based on microPET imaging. The integrin $\alpha_v\beta_3$ receptor specificity was confirmed by blocking experiments for both tracers. Compared with $^{64}$Cu-DOTA-RGD, $^{64}$Cu-AmBaSar-RGD exhibits much lower liver accumulation in both microPET imaging and biodistribution studies.

ABBREVIATIONS AND NOMENCLATURE

The IUPAC names for the cage ligands of the present invention and metal complexes of the cage compounds are long and complicated. The names for the ligands described or discussed herein are abbreviated as follows:

3,6,10,13,16,19-hexaazabicyclo[6.6.6]icosane is referred to "sarcophagine", or "Sar";

1,8-Diamine-3,6,10,13,16,19-hexaazabicyclo[6.6.6]icosane is referred to as "Diamsar";

1-N-(4-aminobenzyl)-3,6,10,13,16,19-hexaazabicyclo[6.6.6]icosane-1,8-diamine is referred to as "SarAr";

Methyl 4-((8-amino-3,6,10,13,16,19-hexaazabicyclo[6.6.6]icosane-1-ylamino)methyl)benzoate is referred to as "AmMBSar"; and 4-((8-amino-3,6,10,13,16,19-hexaazabicyclo[6.6.6]icosane-1-ylamino)methyl)benzoic acid is referred to as "AmBaSar";

1,4,7,10-tetraazacyclododecane-N,N',N'',N'''-tetraacetic acid is referred to as DOTA, and 1,4,8,11-tetraazacyclotetradecane-N,N',N'',N'''-tetraacetic acid is referred to as TETA.

Unless otherwise indicated, complexes described herein are named using a nomenclature which represents these M-hexaamine cage complexes by "M-(A, Bsar)", where M represents metal ion, and A and B are the substituents in the 1- and 8-positions of the Sar cage:

(1,8-Dinitro-Sar)cobalt(III)trichloride is represented by the chemical formula [Co(DiNosar)]Cl$_3$;

(1,8-Diamine-Sar)cobalt(III)pentachloride is represented by the chemical formula [Co(DiAmSar)]Cl$_5$;

(1,8-Diamine-Sar)copper(II)tetrachloride is represented by the chemical formula [Cu(DiAmSar)]Cl$_4$;

(1-amine, 8-(aminomethyl) 4'-methylbenzoate-Sar)copper (II) is represented by the chemical formula [Cu(AmMBSar)]$^{2+}$;

(1-amine, 8-(aminomethyl-benzoic acid-Sar)copper(II) is represented by the chemical formula [Cu(AmBaSar)]$^{2+}$;

(1,8-(aminomethyl) 4'-methylbenzoate-Sar)copper(II) is [Cu(DiAMBSar)]$^{2+}$.

Design, Synthesis, and Characterization of Bifunctional Chelator AmBaSar

In order to design a suitable bifunctional chelator for $^{64}$Cu labeling and conjugating with RGD, it was necessary to modify the linkage of diamsar. The aromatic amine of SarAr can be replaced with an aromatic carboxyl, which can conjugate a cyclic peptide containing the RGD motif in addition to a lysine for conjugating to the chelator, to form BFC AmBaSar. AmBaSar can efficiently label $^{64}Cu^{2+}$ due to the provision of a three-dimensional hexa-aza cage which increases thermodynamic and kinetic stability to complex $^{64}Cu^{2+}$ or other metal ions, while allowing the aromatic linker with carboxyl acid group to conjugate with the amine of lysine in the cyclic peptide containing the RGD motif. The AmBaSar-RGD can be used to form new nuclear, MRI, and optical probes by complexion with other appropriate metal radioisotopes or paramagnetic metal ions using similar preparations. Appropriate metals include, but are not limited to $^{90}Y$, Gd, $^{68}Ga$, $^{57/60}Co$, $^{52}Fe$ and $^{64/67}Cu$.

AmBaSar can be reacted with a variety of peptides or biomolecules, since the chemistry for conjugating AmBaSar to other peptides is similar to that described for the cyclic peptide RGD. The identity of the peptides is not particularly limited as long as pendant carboxylate group or carboxylic acid group of the AmBaSar chelator be directly conjugated to an amine of a lysine or N-terminal in the peptide. Preferably however, the peptide is to which AmBaSar is reacted is one that targets a specific biomolecule. Other peptides include, but are not limited to, Asp-Gly-Glu-Ala (DGEA) (SEQ ID NO: 1), bombesin peptides (BBN), uPAR peptides, and other peptides with a lysine amine or N-terminal.

Figure 1:
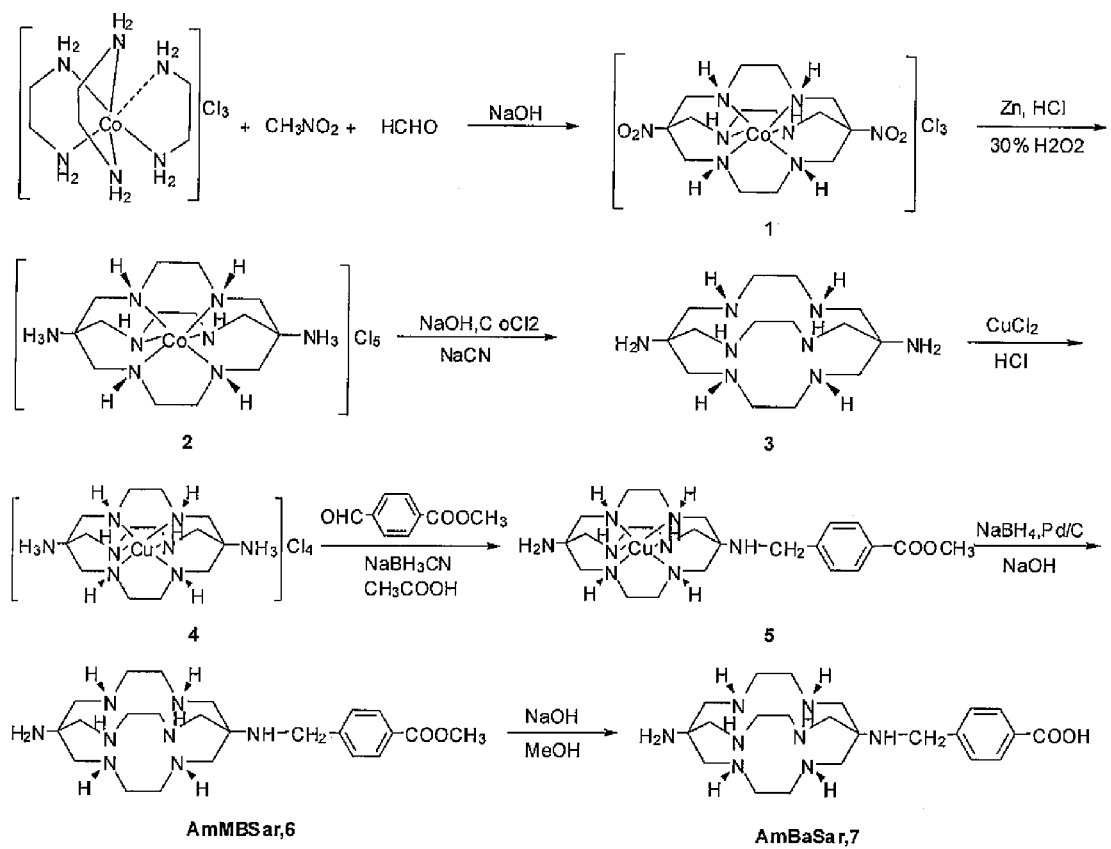
FIG. 1 is a chart depicting a procedure for the synthesis of the bifunctional chelator AmBaSar

An efficient synthesis of AmBaSar is shown in FIG. 1. The degree of hydration of the synthesized compounds is dependent on the method of purification. FIG. 1, Compounds 1~4 may be prepared based on methods described in the literature using cobalt complexes as starting materials, (Refs. 14, 15) However, the reported syntheses of compound 1~4 are incomplete and with compounds not fully characterized. The comprehensive synthetic methods and full characterization of these compounds are disclosed herein.

In brief, and as shown in FIG. 1-1, tris(ethylenediamine) cobalt(III) chloride initiates the encapsulation process using the reactive nucleophile nitromethane and formaldehyde in alkaline solution at room temperature to form a hexa aza cage containing Co(III) compound 1, which was then reduced with zinc dust in acid solution to give the very stable Co(III) diamsar complex 2. The Co(III) ion of compound 2 can be removed by reduction with high concentrations of hydrochloric or hydrobromic acid at high temperatures (130~150° C.) or excess cyanide ion to yield the free cage. Here we used excess cyanide ion to remove the metal ion in compound 2 to form compound 3 in good yield (58.5%). The six nitrogen donor atoms of the hexa aza cage allows strong binding to many metal ions, such as $Cu^{2+}$, so compound 3 was easy to complex with metal ion $Cu^{2+}$, yielding compound 4 under weak acid conditions. The compounds 1~4 were characterized by elemental analysis, MS and $^1H$-NMR, the results are consistent with literature reports. (Refs. 14, 15.)

It is difficult to functionalize the apical primary amines of diamsar 3 (FIG. 1) directly because there are 2 primary and 6 secondary amines in diamsar, which potentially could create many by-products and difficulty during purification. The initial formation of copper(II) complex of diamsar 4 (FIG. 1) ties up the 6 secondary amines of diamsar, and also permit the tracking of the resultant Cu(II) complexes on the ion exchange columns. (Ref. 16.) Structural studies have confirmed that it is possible to exploit the relatively low nucleophilicity of the Cu(II) complex of diamsar in acylation and alkylation reactions leading to a variety of functionalized cage amine complexes. (Refs. 17, 18). The hydride reducing agent sodium cyanoborohydride ($NaBH_3CN$) is used for reduction due to its stability in relatively strong acid solutions (about pH 3), its solubility in hydroxylic solvents such as ethanol, and its different selectivities at different pH values. At pH 3~4 it reduces the imine to an amine efficiently, while this reduction becomes very slow at higher pH values. (Ref. 19) The reducing reaction of the cage amine of compound 4 with aromatic methyl 4-formylbenzoate under $NaBH_3CN$ ethanol acid solution yields aromatic functionalization of the cage amine compound 5 and the by-product bis-4-formylbenzoate diamsar complex. This reaction took a significant amount of time (4 days) and yield was 27.9% due to low nucleophilicity. Separation was carried out by ion exchange chromatography. Compound 6 was achieved by demetallation of compound 5, followed by alkaline hydrolysis to produce the target compound 7 AmBaSar according to the reported method. (Ref. 20)

AmBaSar Conjugating Cyclic Peptide RGD and $^{64}Cu$ Radiolabeling:

AmBaSar contains one carboxyl group and an inactive primary amine, which means that it is a mono-functional molecule that can react with a cyclic peptide containing the RGD motif in addition to a lysine for conjugating to the chelator. Literature methods may be used for conjugation of the cyclic RGD with AmBaSar and preparing $^{64}Cu$ radiolabeled conjugates. (Refs. 6, 21, 22)

Figure 2:
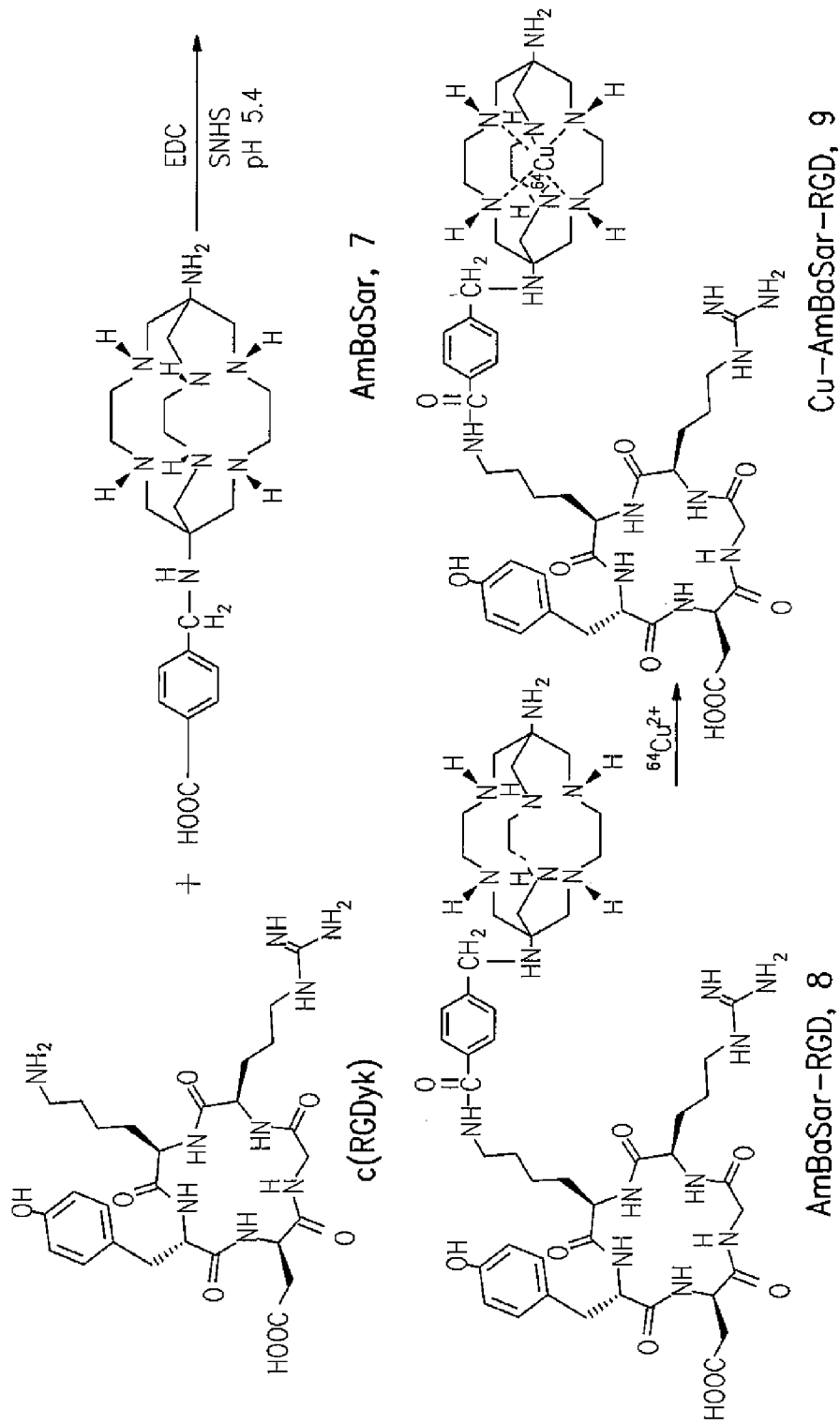
FIG. 2 is a chart depicting a procedure for the synthesis of AmBaSar-RGD and labeled with Copper-64.

FIG. 2 is a chart showing the method for AmBaSar conjugating cyclic RGD and $^{64}Cu$ radiolabeling. The cyclic RGD conjugate AmBaSar-RGD was synthesized in 80% yield and purified by semipreparative HPLC. Analytical HPLC found the retention time of AmBaSar-RGD to be 3.8 min, whereas cyclic RGD peptide eluted at 25 min under the same condition. AmBaSar-RGD was analyzed by mass spectrometry. found m/z=1049.3 for $[M+H]^+$ ($M=C_{50}H_{80}N_{16}O_9$) and 1089.7 for $[M+K]^+$.

In another embodiment of the present invention, the peptide-chelator conjugate AmBaSar-RGD can be complexed with $^{64}Cu$ to form a new PET tracer for imaging the $\alpha_v\beta_3$ integrin receptor. AmBaSar-RGD was labeled with $^{64}Cu$ in 0.1 M ammonium acetate (pH 5.0) solution at room temperature (25° C.) for 1 h. The free $^{64}Cu$-acetate was eluted at 3.2 min, while $^{64}Cu$-AmBaSar-RGD was eluted at 15.8 min by analytical HPLC, which was confirmed by cold Cu-AmBaSar-RGD. The radiochemical yield obtained was ≥80% and the radiochemical purity was ≥95%.

EXPERIMENTAL

Methods and Materials:

$^1H$ NMR spectra were obtained using a Varian Mercury 400 MHz instrument (USC NMR Instrumentation Facility), and the chemical shifts were reported in ppm on the δ scale relative to an internal TMS standard. Microanalyses for carbon, hydrogen, nitrogen and chlorine, cobalt, copper were carried out by the Columbia Analytical Services, Inc (Tucson, Ariz.). Mass spectra using LC-MS were operated by the Proteomics Core Facility of the USC School of Pharmacy. Thin-layer chromatography (TLC) was performed on silica gel 60 F-254 plates (Sigma-Aldrich) using a mixture solution of 70% MeOH and 30% aqueous $NH_4OAc$ ($NH_4OAc$ solution is 20% by weight) as the mobile phase. Ion-exchange chromatography was performed under gravity flow using Dowex 50 WX2 ($H^+$ form, 200-400 mesh) or SP Sephadex C25 ($Na^+$ form, 200-400 mesh) cation exchange resins. All evaporations were performed at reduced pressure (ca. 20 Torr) using a Büchi rotary evaporator.

HPLC was accomplished on two Waters 515 HPLC pumps, a Waters 2487 absorbance UV detector and a Ludlum Model 2200 radioactivity detector, operated by Waters Empower 2 software. Purification of the conjugate AmBaSar-RGD was performed on a Phenomenex Luna C18 reversed phase column (5 μm, 250×10 mm); the flow was 3.2 mL/min, with the mobile phase solvent A (12% acetonitrile in water), and the absorbance monitored at 254 nm. The analytical HPLC was done on a Phenomenex Luna C18 reversed phase column (5 μm, 250×4.6 mm) and monitored using a radiodetector and UV at 218 nm. The flow was 1.0 mL/min, with the mobile phase starting from 99% solvent B (0.1% TFA in water) and 1% solvent C (0.1% TFA in acetonitrile) (0~1 min) to 70% solvent B (0.1% TFA in water) and 30% solvent C (0.1% TFA in acetonitrile) (1~30 min).

All reagents and solvents were purchased from Sigma-Aldrich Chemicals (St. Louis, Mo., USA) and used without further purification unless otherwise stated. N-hydroxysulfosuccinimide sodium salts (SNHS) and N-ethyl-N'-(3-dimethylaminopropyl) carbodiimide hydrochloride (EDC.HCl) were obtained from the Sigma-Aldrich Chemical Co. The cyclic RGDyK peptide was purchased from Peptides International, Inc (Louisville, Ky., USA). $^{64}CuCl_2$ was purchased from MDS Nordion (Vancouver, BC, Canada). Water was purified using a Milli-Q ultra-pure water system from Millipore Corp. (Milford, Mass., USA).

Experimental: AmBaSar Synthesis and Characterization

Synthesis of [Co(DiNoSar)]Cl$_3$ (1)

To a solution of tris(ethylenediamine)cobalt(III) chloride dehydrate (1.2 g, 3.0 mmol) in water (4.0 mL) was added nitromethane (0.7 g, 12 mmol) and aqueous formaldehyde (37%, 2.4 g, 30 mmol). The resulting solution was cooled to 4° C. on an ice-water bath. Aqueous NaOH (4.0 M, 3.0 mL) was cooled to 4° C. and mixed with the resulting solution above. The combined solution was stirred on ice-water bath where it rapidly turned deep violet-brown from the initially orange color, and the reaction temperature was allowed to raise to room temperature 23-25° C. After 90 min, the reaction was quenched by the addition of HCl (6.0 M, 2.0 mL). The orange precipitate formed was collected by filtration after cooling on ice for 2 h, washed with methanol, and dried to provide 1 (1.46 g, 90.2%). $^1$H-NMR (D$_2$O): δ 3.55-3.65 (d, 6H, NCCH$_2$N); 3.15-3.35 (d, 6H, NCCH$_2$N); 3.00-3.10 (d, 6H, NCH$_2$CH$_2$N); 2.55-2.65 (d, 6H, NCH$_2$CH$_2$N). MS: Calcd for $C_{14}H_{31}CoN_8O_4$ [M+1-3 HCl]$^+$ m/z 431.2. found 431.5. Elemental analysis calculated for $C_{14}H_{30}Cl_3CoN_8O_4$, requires C, 31.15; H, 5.60; N, 20.76; Cl, 19.71; Co, 10.92. Found: C, 30.90; H, 5.46; N, 20.13; Cl, 20.80; Co, 10.70.

Synthesis of [Co(DiAmSar)]Cl$_5$.H$_2$O (2).

[Co(DiNoSar)]Cl$_3$ (2.0 g, 3.7 mmol) was dissolved in deoxygenated water (100 mL) under N$_2$ atmosphere. Zinc dust (2.3 g, 35 mmol) was added into the solution with stirring for 5 min, followed by addition of HCl (6 M, 15 mL) dropwise. The resulting solution confirmed to stir for an additional 60 min under N$_2$ atmosphere. The N$_2$ flow was stopped and 30% H$_2$O$_2$ (1.0 mL) was added. The resulting solution was warmed for 15 min on 75° C. water bath, then cooled and placed on a Dowex 50 WX2 cation exchange column and washed with water (120 mL), followed by HCl (1.0 M, 120 mL). The complex was then eluted with HCl (3.0 M, 400 mL) and the yellow eluate was collected and dried under vacuum to yield 2 (1.78 g. 87%). $^1$H-NMR (D$_2$O): δ 3.30-3.10 (m, 12H, NCCH$_2$N); 2.50-2.65 (m, 12H, NCH$_2$CH$_2$N). MS Calcd for $C_{14}H_{35}CoN_8$ [M+1-5 HCl—H$_2$O]$^+$ m/z 371.2. found 371.7. Elemental analysis calculated for $C_{14}H_{38}Cl_5CoN_8O$, requires C, 29.46; H, 6.71; N, 19.63; Cl, 31.06; Co, 10.33. Found: C, 29.06; H, 6.73; N, 19.04; Cl, 25.30; Co, 9.50.

Synthesis of Diamsar.5H$_2$O (3)

Co(DiAmSar)]Cl$_5$.H$_2$O (3.58 g, 6.3 mmol), NaOH (0.58 g, 14.5 mmol, sufficient to neutralize the protonated primary amino groups) and Cobalt(II) chloride hexahydrate (1.6 g, 6.4 mmol) were dissolved in deoxygenated water (50 mL) under nitrogen. Sodium cyanide (5.60 g, 114 mmol) was added to the resulting solution. The reaction mixture was heated to 70° C. being stirred under nitrogen until the solution had become almost colourless (overnight). This final solution was taken to dryness under vacuum, with the residue extracted with boiling acetonitrile (3×25 mL). The total extract was filtered, reduced under vacuum to a white solid, and cooled to −10° C. to precipitate white crystals of the product. Drying in vacuo provided 3 (1.72 g, 58.5%). mp 91~94.0° C. $^1$H-NMR (D$_2$O): δ 2.51 (s, 12H, NCCH$_2$N); 2.42 (s, 12H, NCH$_2$CH$_2$N). MS Calcd for $C_{14}H_{35}N_8$ [M+1-5H$_2$O]$^+$ m/z 315.3. found 315.8. Elemental analysis calculated for $C_{14}H_{44}N_8O_5$, requires C, 41.56; H, 10.96; N, 27.70. Found: C, 41.53; H, 10.28; N, 27.12.

Synthesis of [Cu(DiAmSar)]Cl$_4$.5H$_2$O (4).

CuCl$_2$.2H$_2$O (0.17 g, 1.0 mmol), was dissolved in 10 mL water, following added 3 (0.41 g, 1.0 mmol). The solution was acidified to pH=4.0 with HCl (0.1 M), and stirred overnight. Evaporation on heating yielded a blue precipitate. The blue solid was cooled, filtered, and washed with ethanol (5 mL×3), and dried, yielding a blue crystalline product 4 (0.53 g, 97%). $^1$H-NMR (D$_2$O): δ 3.20 (s, 12H, NCH$_2$CH$_2$N); 2.90 (s, 12H, NCCH$_2$N). MS Calcd for $C_{14}H_{33}CuN_8$ [M+1-4 HCl-5H$_2$O]$^+$ m/z 376.2. found 376.0. Elemental analysis calculated for $C_{14}H_{46}Cl_4CuN_8O_5$, requires C, 27.48; H, 7.58; N, 18.31; Cl, 23.17; Cu, 10.38. Found: C, 27.72; H, 7.17; N, 17.87; Cl, 22.40; Cu, 9.71.

Synthesis of [Cu(AmMBSar)](CH$_3$COO)$_2$.5H$_2$O (5)

[Cu(DiAmSar)]Cl$_4$.5H$_2$O (0.73 g, 1.2 mmol) was dissolved in dry ethanol (30 mL), followed by addition of methyl 4-formylbenzoate (0.28 g, 1.7 mmol), dried/activated 4 Å molecular sieves (1.0 g) and glacial acetic acid (60 μL). The resulting solution was stirred for 3 h under argon gas, followed by addition of sodium cyanoborohydride (0.82 g, 14 mmol). The reaction mixture continued to stir under argon gas for 4 days at room temperature 20~25° C. The mixture was filtered, and filtrate was evaporated to dryness and extracted with ethyl acetate (15 mL×3), dried and then diluted to 300 mL. It was placed onto a SP Sephadex C25 column and eluted with sodium citrate (0.1 M, 400 mL) and a wide blue band formed. Increasing the sodium citrate concentration (0.3 M, 500 mL) resulted in three blue bands eluting in order as [Cu(diamsar)]$^{2+}$, [Cu(AmMBSar)]$^{2+}$ (compound 5), and [Cu(DiAMBSar)]$^{2+}$ by TLC monitoring. The second band eluate (compound 5 solution, 100 mL) was isolated and diluted with water (10 fold, 1.0 L), and placed onto another SP Sephadex C25 column. A single blue band eluted with sodium acetate (1.0 M, 200 mL), was evaporated to dryness and the residue extracted with 2-propanol (50 mL×3). Fine white crystals of sodium acetate were separated, filtered and the process of evaporation and extraction repeated 3 times. The final residue was dried in vacuo to a dark blue solid 5 [Cu(AmMBSar)](Ac)$_2$.5H$_2$O (246.5 mg, 27.9%). $^1$H-NMR (D$_2$O): δ 8.0-7.9 (d, 2H, aromatic); 7.48-7.42 (d, 2H, aromatic); 4.70 (s, 3H, OCH$_3$); 4.02 (s, 2H, CH$_2$—Ar); 3.54-3.30 (m, 12H, NCH$_2$CH$_2$N); 2.93-2.78 (m, 12H, NCCH$_2$N). MS Calcd for $C_{23}H_{43}CuN_8O_2$ [M+1-2 HAc-5H$_2$O]$^+$ m/z 526.3. found 526.8.

Synthesis of AmMBSar (6)

Sodium borohydride (150 mg) was dissolved in 0.4 mL water and stirred under a nitrogen atmosphere, following addition of Pd/C (60 mg) in 1.0 mL water. Compound 5 (164 mg) was dissolved in sodium hydroxide (3 mL; 1% NaOH) and added dropwise to the above mixture solution. Stirring was continued under nitrogen at 25° C. until the color turned from blue to clear. The resulting solution was filtered (0.22 µm) and the filtrate collected in an ice-cooled glass vial. Concentrated hydrochloric acid was added dropwise (50 µL) to the cooled solution until gas evolution ceased (~450 µL, HCl). The solution was acidified to pH 4~6, and then dried under vacuum to provide AmMBSar, 6 (56 mg, 47.6%). $^1$H-NMR (D$_2$O): δ 7.97-7.92 (d, 2H, aromatic); 7.50-7.45 (d, 2H, aromatic); 4.65 (s, 3H, OCH$_3$); 4.08 (s, 2H, CH$_2$—Ar); 3.45-3.20 (m, 12H, NCH$_2$CH$_2$N); 3.12-2.98 (m, 12H, NCCH$_2$N); 1.98~1.85 (m, 9H, NH). MS Calcd for C$_{23}$H$_{42}$N$_8$O$_2$[M+1]$^+$ m/z 463.0. found 462.8.

Synthesis of AmBaSar (7)

Figure 3:
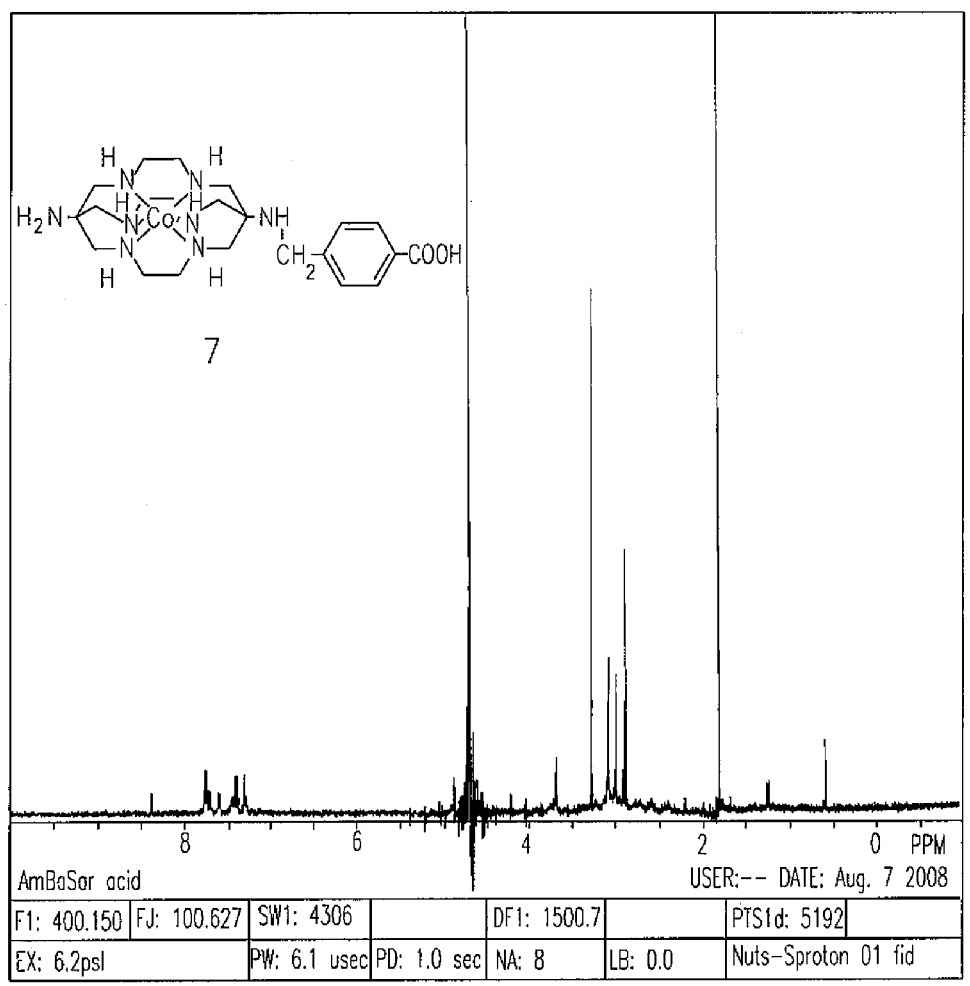
FIG. 3 is a, representative $^1$H-NMR spectra in $D_2O$ of AmBaSar.
Figure 4:
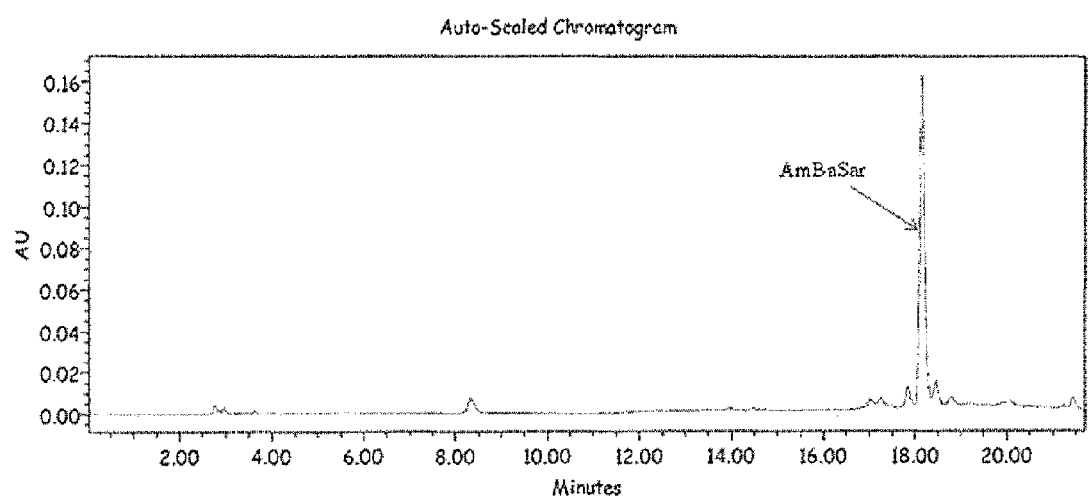
FIG. 4 is a representative HPLC chromatogram of AmBaSar.

Compound 6 (46.2 mg, 0.1 mmol) was dissolved in methanol (3 mL) and water (1.0 mL), followed by addition of NaOH (1.5 mL, 0.1 M). The resulting solution was refluxed and stirred for 5 h, then neutralized with HCl (1.0 M) to pH 6~7. Drying the solution under reduced pressure formed solids, which were dissolved with hot MeOH (3×2 mL). The total extract was filtered and dried under vacuum to yield AmBaSar, 7 (36 mg, 80.2%). $^1$H-NMR (D$_2$O): δ 7.76-7.67 (m, 2H, aromatic); 7.45-7.37 (m, 2H, aromatic; 3.66 (s, 2H, NCH$_2$C) 3.26-3.04 (m, 12H, NCCH$_2$N); 2.99-2.84 (m, 12H, NCH$_2$CH$_2$N); 1.84-1.77 (m, 9H, NH). MS Calcd for C$_{23}$H$_{42}$N$_8$O$_2$ [M+1]$^+$ m/z 449.3. found 449.7. A typical $^1$H-NMR spectra of AmBaSar in D2O is shown in FIG. 3. A Typical HPLC chromatogram of AmBaSar using the Analytical HPLC system is shown in FIG. 4.

Synthesis of Other Carboxylic Acid functionalized Sar Based bifunctional chelators. Although the methodology for functionalizing the apical amine has been described primarily with respect to AmBaSar, Sar may be functionalized with other carboxylic acids by reacting with the compounds that have an aldehyde on one side and the Methoxyl ester on the other. These two groups could located at different positions of an aromatic system (including those with hetro-atoms), aliphatic system (including those with double or triple bonds), or the combination of those two.

Figure 21:
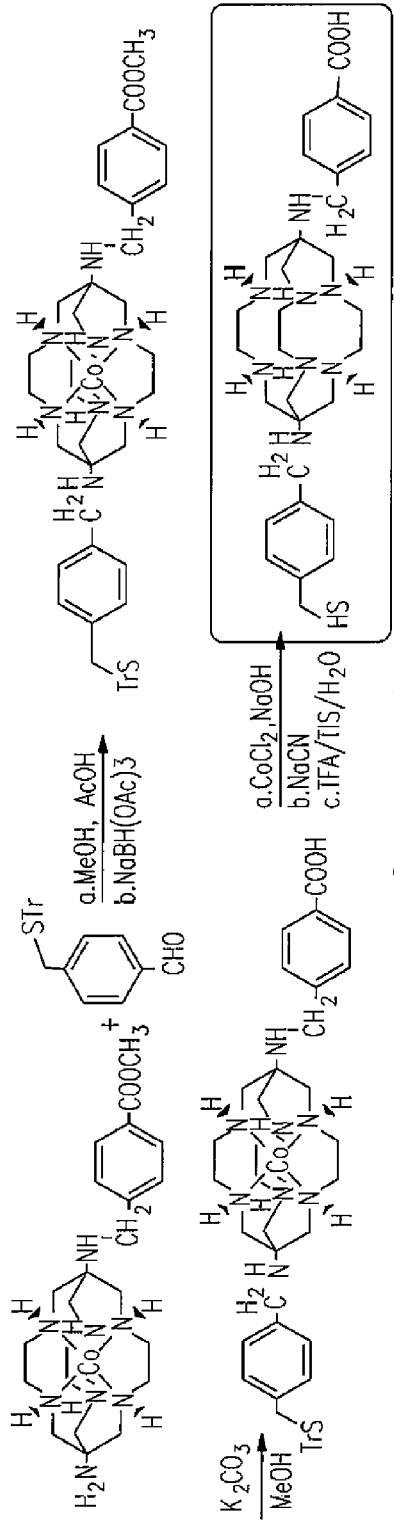
FIG. 21 is a chart showing a synthetic method for the preparation of thiol and carboxylate functionalized BFCs according to the present invention.

Synthesis of Carboxylate and Thiol Functionalized Sar Based Bifunctional Chelators:

Using methods analogous to the preparation of AmBaSar, the carboxylate and thiol functionalized Sar cage is synthesized by a method shown in FIG. 21. Starting from the monosubstituted Sar cage and commercially available agents, a bifunctional linker with protected thiol and carboxylate groups is obtained. After the removal of the Co metal and deprotection, the carboxylate and thiol functionalized Sar cage is obtained. Various linkers may also be introduced to this Sar cage agent.

Figure 22:
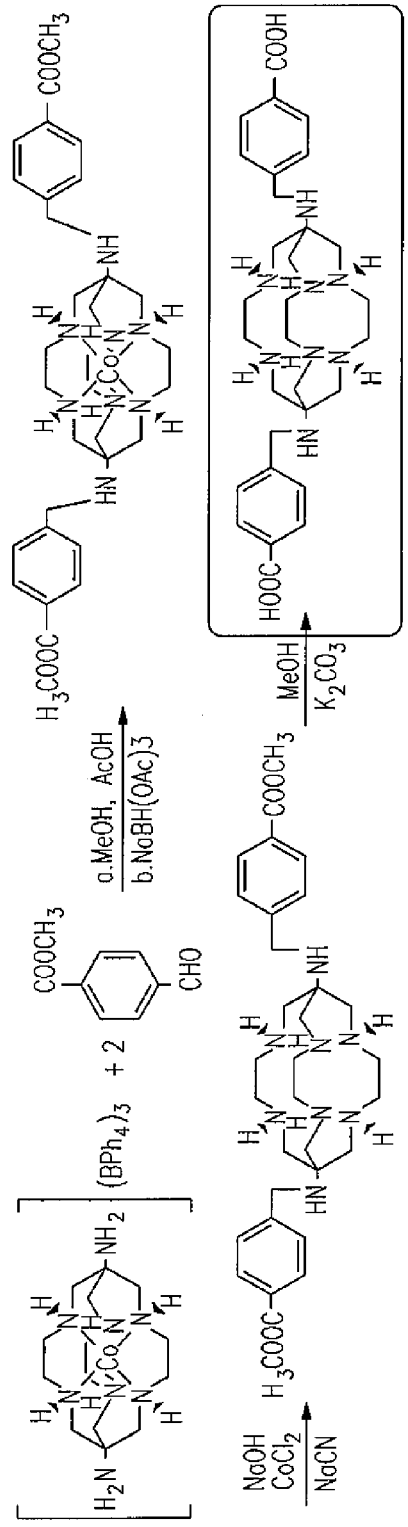
FIG. 22 is a chart showing a synthetic method for the preparation of DiBaSar according to the present invention.

Synthesis of DiBaSar and Functionalized Sar Based Bifunctional Chelators Having Carboxylic Acid Groups at Both Apical Amines DiBaSar and Sar based structures functionalized with carboxylic acids at both apical amines may be synthesized by a synthetic procedure described in FIG. 22

Experimental

AmBaSar Conjugating Peptide RGD and Radiolabeling

Synthesis of AmBaSar-RGD (8, FIG. 2)

Figure 5:
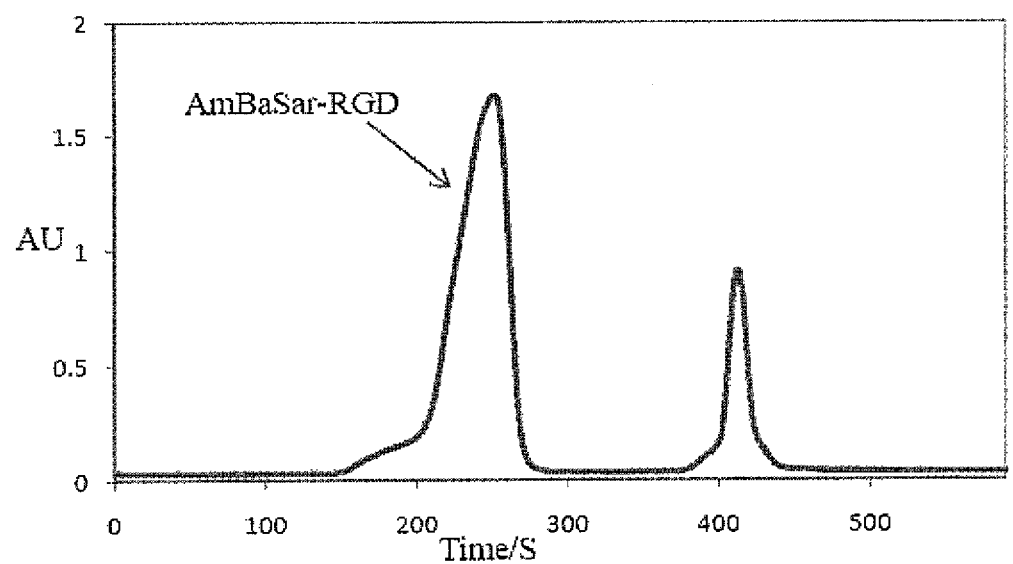
FIG. 5 a representative chromatogram of crude AmBaSar-RGD using the semipreparative HPLC system.
Figure 6:
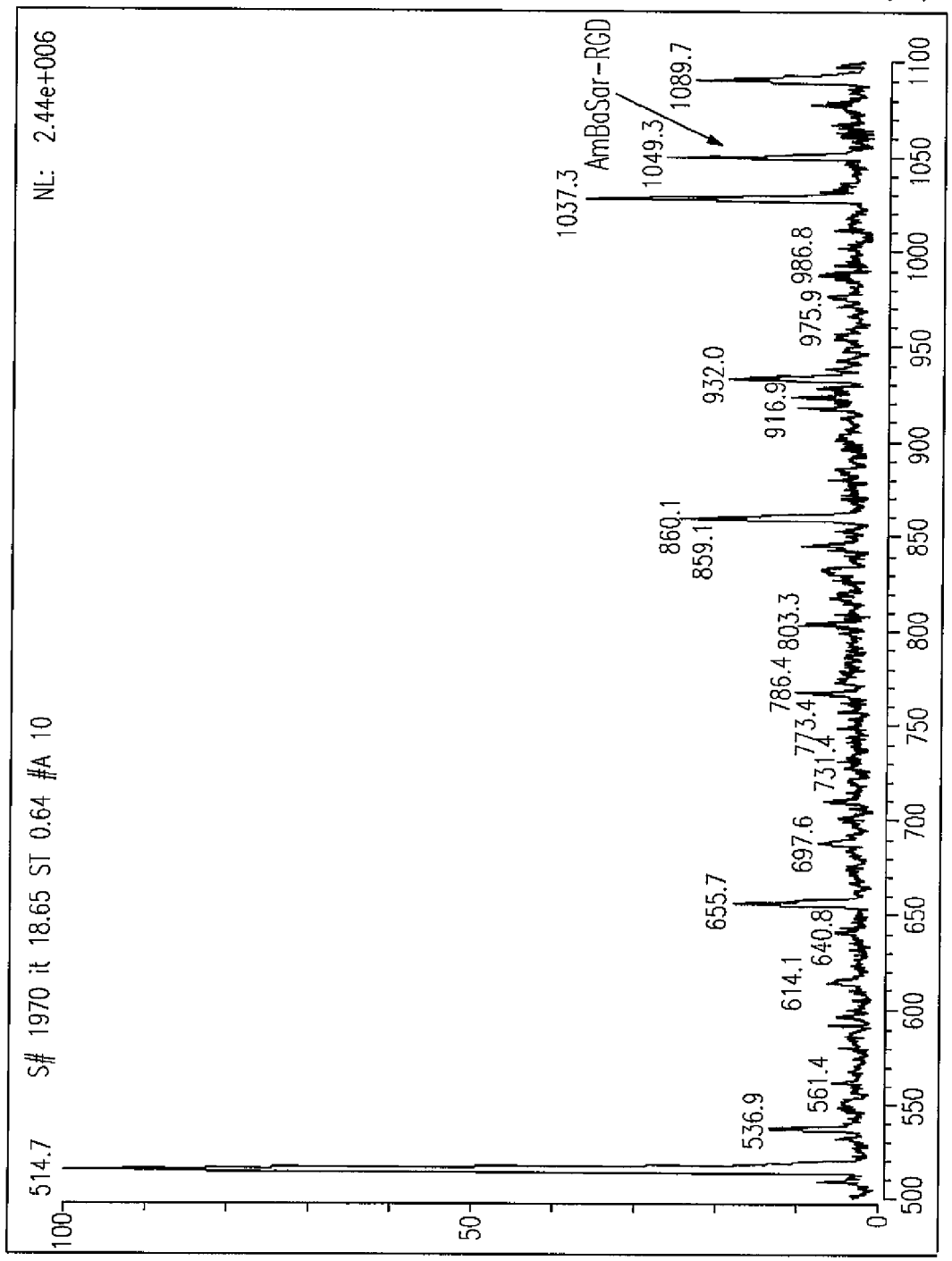
FIG. 6 is a representative mass spectra of AmBaSar-RGD

AmBaSar was activated by EDC at pH 5.5 for 30 min (4° C.), with a molar ratio of AmBaSar:EDC:SNHS=5:5:4. Typically, 15.0 mg of AmBaSar (30 µmol) was dissolved in 500 µL, of water. Separately, 5:76 mg of EDC (30 µmol) was dissolved in 500 µL of water. The two solutions were mixed, and 0.1 M NaOH (250 µL) was added to adjust the pH to 4.5. SNHS (5.2 mg, 24 µmol) was then added to the stirring mixture on an ice-bath, followed by 0.1 M NaOH (50 µL) to finalize the pH to 5.4. The reaction was allowed to stir for 30 min at 4° C. The theoretical concentration of active ester AmBaSar-OSSu was calculated to be 24 µmol. Cyclic RGD peptide (2.5 mg, 4.0 µmol) dissolved in 500 µL (5.0 mg/mL) of water was cooled to 4° C. and added to the AmBaSar-OSSu reaction mixture. The pH was adjusted to 8.6 with 0.1 M NaOH (280 µL). The reaction was allowed to proceed overnight at room temperature (20~25° C.). The AmBaSar-RGD conjugate was purified by semipreparative HPLC. A representative chromatogram of the AmBaSar-RGD is shown in FIG. 5. The peak containing the RGD conjugate was collected, lyophilized, and dissolved in water at a concentration of 1.0 mg/mL for use in radiolabeling reactions. A mass spectra of AmBaSar-RGD is shown in FIG. 6.

Synthesis of [Cu-AmBaSar-RGD](Ac)$_2$.2HAc.

The AmBaSar-RGD (1.0 mg) was dissolved in 0.5 mL of a 0.1 M ammonium acetate/0.80 mM copper (II) acetate solution. The mixture was stirred at 37° C. for 40 min and allowed to cool to room temperature. The crude Cu-AmBaSar-RGD solution was purified and quantified by HPLC. MS Calcd for C$_{58}$H$_{94}$N$_{16}$O$_{17}$Cu [M+1]$^+$ m/z 1352.0. found 1351.9.

Radiolabeling of $^{64}$Cu-AmBaSar-RGD.

Figure 7:
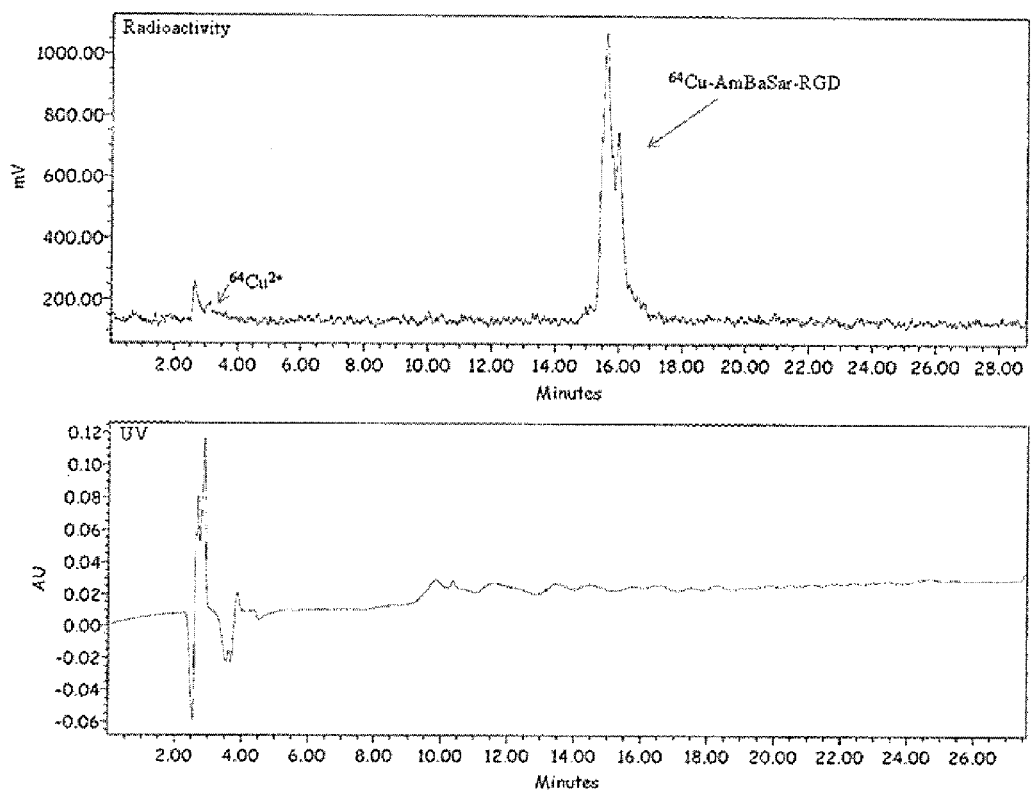
FIG. 7 is representative radio-HPLC chromatogram of crude $^{64}$Cu-AmBaSar-RGD using the analytical HPLC system described herein.

[$^{64}$Cu]Acetate ($^{64}$Cu(OAc)$_2$) was prepared by adding 111 MBq (3 mCi) of $^{64}$CuCl$_2$ in 0.1 M HCl into an 1.5 mL microfuge tube containing 300 µL 0.1 M ammonium acetate (pH 5.0), followed by mixing using a mini vortex and incubating for 15 min at room temperature. The AmBaSar-RGD (1-2 µg in 100 µL 0.1 M ammonium acetate) was labeled with $^{64}$Cu(OAc)$_2$ by addition of 1-3 mCi of $^{64}$Cu. The chelation reaction was performed in 0.1 M sodium acetate buffer, pH 5.0, for 60 min at room temperature (23~25° C.). Labeling efficiency was determined by HPLC. $^{64}$Cu-AmBaSar-RGD was purified by radio-HPLC. The elute was evaporated and the activity reconstituted in saline, followed by passage through a 0.22 µm Millipore filter into a sterile dose vial for use in animal experiments. A representative radio-HPLC chromatogram of $^{64}$Cu-AmBaSar-RGD is shown in FIG. 7.

Improved Synthesis of AmBaSar

Figure 8:
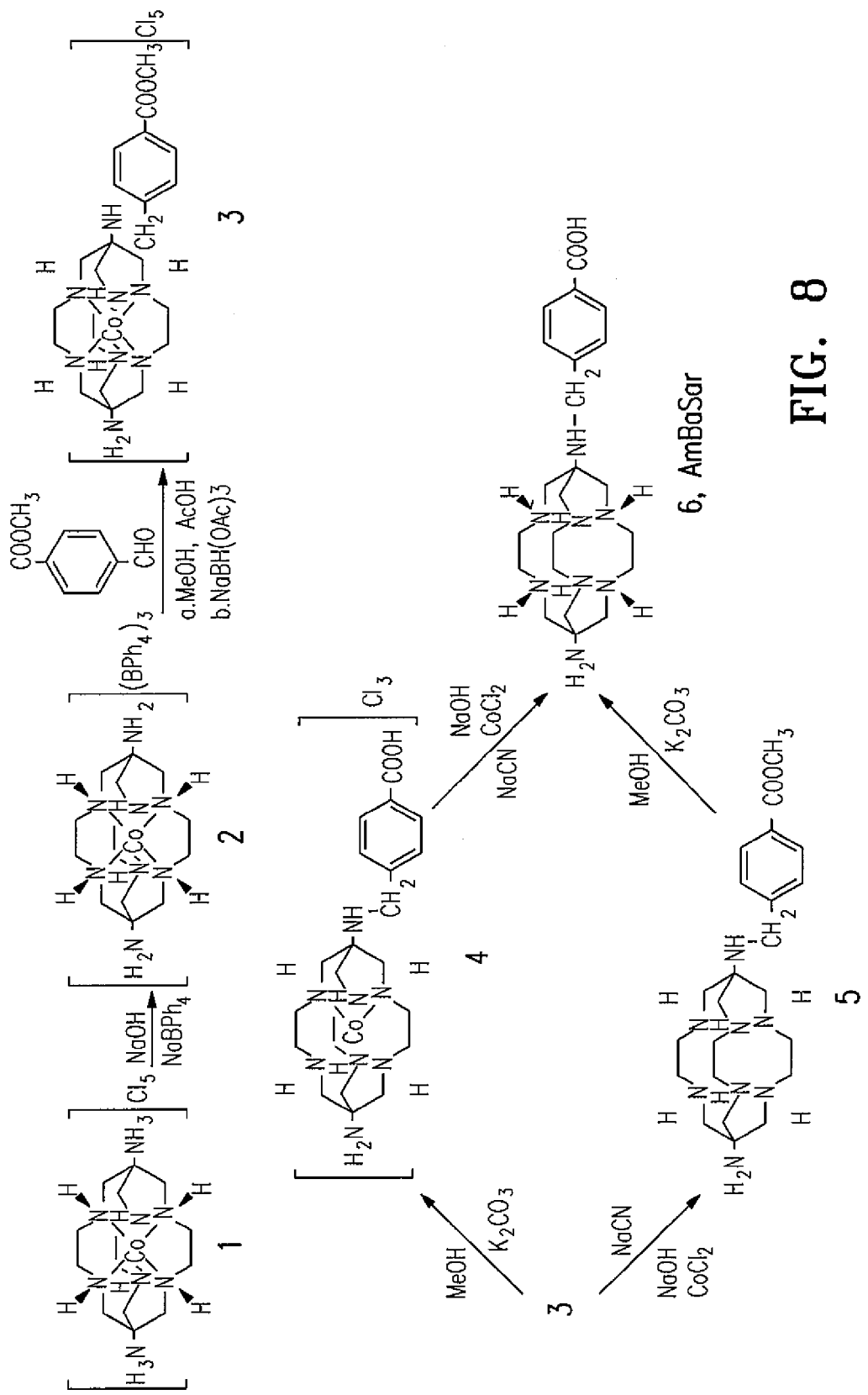
FIG. 8 shows a synthesis scheme for an improved method of synthesizing the bifunctional chelator AmBaSar.

Another embodiment of the present invention is directed to an improved synthetic route of AmBaSar. The improved synthesis of the BFC AmBaSar is shown in FIG. 8. In this new synthetic route, AmBaSar is obtained in only four steps starting from Co(DiAmSar)]Cl$_5$ (1). As shown in FIG. 8, Compound 1 was transformed to the 3 Cl salt by neutralizing the protonated primary amino groups with NaOH, which was then converted to the tetraphenylborate salt compound 2 by anion exchange of [Co(DiamSar)]Cl$_3$ with sodium tetraphenylborate (NaBPh$_4$) in aqueous solution. (Ref. 24) The coupling of the aldehyde to the amine of compound 2 yielded aromatic functionalization of the cage compound 3 Co(AmBMSar) complex. This reaction was carried out under dehydrating and refluxing conditions before adding the reducing agent according to literature method. (Ref. 24) Molecular sieves 4 Å were employed to remove the water produced in the formation of the iminium ion. Compared with the Cu complex (27.9% yield), we also observed an increased yield (39.1% yield) in this step, which could be partially attributed to the preferable solubility of the tetraphenylborate salt compared with the chloride salt in methanol. We also found that AmBaSar could be made in two ways from compound 3. One method was similar to that discussed herein, where the Co(III) ion of compound 3 was removed by excess cyanide ion to yield the free cage compound 5 AmBMSar, which then was hydrolyzed to produce the target compound 6

AmBaSar. Another method employed alkaline hydrolysis of compound 3 first, with subsequent removal of cobalt ion to yield the AmBaSar (6).

This improved synthesis of AmBaSar shortens synthetic steps and simplifies purification. The improved synthesis also simplified the separation process and increased the yield. The overall yield was increased to about 6.0±0.2% (n=6) compared with the original 4.7% by using tris(ethylenediamine) cobalt(III) chloride dehydrate as starting material.

Materials.

All reagents and solvents were purchased from Sigma-Aldrich Chemicals (St. Louis, Mo., USA) and used without further purification unless otherwise stated. DOTA was purchased from Macrocyclics (Dallas, Tex., USA). $^{64}CuCl_2$ was ordered from MDS Nordion (Vancouver, BC, Canada). Compound 1 (Co(DiAmSar)]$Cl_5 \cdot H_2O$) was prepared as described herein. Water was purified using a Milli-Q ultra-pure water system from Millipore Corp. (Milford, Mass., USA).

General Methods:

$^1$H NMR spectra were obtained using a Varian Mercury 400 MHz instrument (USC NMR Instrumentation Facility), and the chemical shifts were reported in ppm on the δ scale relative to an internal TMS standard. Mass spectra using LC-MS were provided by the Proteomics Core Facility of the USC School of Pharmacy. Thin-layer chromatography (TLC) was performed on silica gel 60 F-254 plates (Sigma-Aldrich) using a mixture solution of 70% MeOH and 30% aqueous $NH_4OAc$ ($NH_4OAc$ solution is 20% by weight) as the mobile phase. Ion-exchange chromatography was performed under gravity flow using Dowex 50 WX2 ($H^+$ form, 200-400 mesh) cation exchange resins. All evaporations were performed at reduced pressure (ca. 20 Torr) using a Büchi rotary evaporator.

HPLC was accomplished on two Waters 515 HPLC pumps, a Waters 2487 absorbance UV detector and a Ludlum Model 2200 radioactivity detector, operated by Waters Empower 2 software. The analytical HPLC was performed on a Phenomenex Luna C18 reversed phase column (5 μm, 250×4.6 mm) and monitored using a radiodetector and UV at 254 nm. The flow was 1.0 mL/min, with the mobile phase starting from 99% solvent B (0.1% TFA in water) and 1% solvent C (0.1% TFA in acetonitrile) (0~1 min) to 70% solvent B (0.1% TFA in water) and 30% solvent C (0.1% TFA in acetonitrile) (1~30 min). Radio-TLC was performed with MKC18 silica gel 60 Å plates (Whatman, N.J.) with solvent MeOH/20% NaOAc=3:1 as the eluent using a Bioscan AR2000 imaging scanner (Washington, D.C.) and Winscan 2.2 software.

Synthesis of (1,8-Diamine-Sar)cobalt(III)tri(tetraphenylborate)([Co(DiAmSar)](BPh$_4$)$_3 \cdot H_2O$, 2)

Compound 1 Co(DiAmSar)]$Cl_5 \cdot H_2O$ (3.2 g, 5.5 mmol) was dissolved in water (20 mL), followed by the addition of 2 eq NaOH solution (11.0 mmol, sufficient to neutralize the protonated primary amino groups). The resulting mixture was stirred for 30 min at room temperature until pH was near to 7~8. Sodium tetraphenylborate (5.2 g, 16.5 mmol) in 20 mL methanol was added, and then stirred for 1 h. After filtration and drying under reduced pressure, 6.6 g of compound 2 [Co(DiAmSar)](BPh$_4$)$_3 \cdot H_2O$ (85% yield) was obtained as an orange solid. MS: Calcd for $C_{86}H_{96}B_3CoN_8O$ [M+1-2 HBPh$_4$-H$_2$O]$^+$ m/z 691.7, [M+1-3 HBPh$_4$-H$_2$O]$^+$ 371.4. found 692.1, 371.1. $^1$H-NMR (DMSO-d6): 7.20-6.79 (m, 45H, aromatic); 3.10-2.80 (m, 12H, NCCH$_2$N); 2.60-2.15 (m, 1214, NCH$_2$CH$_2$N).

Synthesis of (1-amine, 8-(aminomethyl) 4'-methylbenzoate-Sar)cobalt(III)pentachloride([Co(AmBMSar)]Cl$_5 \cdot 5H_2O$, 3).

Compound 2 [Co(DiAmSar)](BPh$_4$)$_3 \cdot H_2O$ (7.6 g, 5.7 mmol) was dissolved in anhydrous MeOH (40 mL) and methyl 4-formylbenzoate (1.6 g, 10.0 mmol), followed by addition of 1.7 mL acetic acid and 4 Å molecular sieves. The solution was refluxed 72 h under argon and shielded from visible light. The reaction mixture was cooled to room temperature, and sodium triacetoxyborohydride (NaHB(OAc)$_3$, 9.7 g, 45.0 mmol) was added. The resulting mixture was stirred overnight. The products were loaded onto silica gel and initially purified by flash column chromatography, using a mixture of 70% MeOH and 30% aqueous NH$_4$OAc solution as the eluting solvent. The fractions were monitored by silica gel TLC. This initial column chromatography partially separated the biscoupled Co-cage complex and the mono-coupled Co-cage [Co(AmBMSar)] complex from the starting material. Each product was further purified by evaporating the MeOH, diluting the remaining aqueous solution ~10-fold, and loaded on a Dowex 50-WX2 [H$^+$] cation exchange resin column. The [Co(AmBMSar)] complex was eluted from the column with 3.0-4.0 M HCl. The HCl eluant was evaporated under reduced pressure to give a yellow solid compound 3 [Co(AmBMSar)]Cl$_5 \cdot 5H_2O$ (1.8 g, 39.1% yield). MS: Calcd for $C_{23}H_{54}Cl_5CoN_8O_7$ [M+Na-2 HCl-5H$_2$O]$^+$ m/z 650.2, [M-5 HCl-5H$_2$O+Na]$^+$ 541.2. found 649.7, 541.2. $^1$H-NMR (D$_2$O): 7.93-7.86 (m, 2H, aromatic); 7.42-7.35 (m, 2H, aromatic); 4.05 (s, 3H, CCH$_3$); 3.75 (s, 2H, NCH$_2$C); 3.45-3.26 (m, 12H, NCCH$_2$N); (m, 12H, NCH$_2$CH$_2$N).

Synthesis of (1-amine, 8-(aminomethyl) 4'-carboxybenzene-Sar)cobalt(III)trichloride ([Co(AmBaSar)]Cl$_3 \cdot 5H_2O$, 4).

Compound 3 [Co(AmSarBM)]Cl$_5 \cdot 5$; H$_2$O (2.4 g, 3.0 mmol) was dissolved in the solution of methanol (40 mL)/water (30 mL) containing potassium carbonate (3.0 g), and refluxed for 5 h. The reaction mixture was then neutralized with hydrochloric acid, diluted to 1 L, sorbed on Dowex 50-WX2 [H$^+$] cation exchange resin column, and eluted with hydrochloric acid (2~3 M, 2 L). The dark red fraction was collected and evaporated to dryness. 1.8 g compound 4 was obtained in 89% yield. MS: Calcd for $C_{22}H_{50}Cl_3CoN_8O_7$ [M+Na]$^+$ m/z 724.2, [M+Na-5H$_2$O]*634.2. found 724.1, 634.3. $^1$H-NMR (D$_2$O): 7.91-7.87 (m, 2H, aromatic); 7.42-7.36 (m, 2H, aromatic); 4.00 (s, 2H, NCH$_2$C); 3.47-3.27 (m, 12H, NCCH$_2$N); 3.07-2.73 (m, 12H, NCH$_2$CH$_2$N).

Synthesis of. Methyl 4-(8-amino-3,6,10,13,16,19-hexaazabicyclo[6.6.6]icosane-1-ylamino)methyl)benzoate (AmMBSar, 5).

Compound 3 [Co(AmBMSar)]Cl$_5 \cdot 5$; H$_2$O (790 mg, 1.0 mmol), NaOH (95 mg, sufficient to neutralize the protonated primary amino groups) and CoCl$_2 \cdot 6H_2O$ (260 mg) were dissolved in deoxygenated water (20 mL) under nitrogen. The solution turned green from brown after NaCN (1.0 g) was added. The resulting mixture continued to react in 70° C. under nitrogen until the solution had become almost colourless (overnight). This final solution was evaporated under reduced pressure, and the residue was extracted with boiling acetonitrile (3×15 mL). The total extract was filtered, and dried under vacuum to provided compound 5 AmMBSar (110 mg, 24.5% yield).

Synthesis of AmBaSar (6).

AmBaSar was prepared by two methods:

Method 1. This is similar to the preparation of AmMBSar from compound 3. Briefly, the cobalt ion on compound 4 was removed to produce the target compound 6 AmBaSar (26% yield) by reduction with excess cyanide ion to yield the free cage.

Method 2, Compound 5 was alkaline hydrolyzed to produce the target compound 6 AmBaSar (80.2%, yield).

Radiolabeling of BFC AmBaSar and DOTA, Evaluation of Radiolabeled AmBaSar and Comparison with Radiolabeled DOTA.

Figure 9:
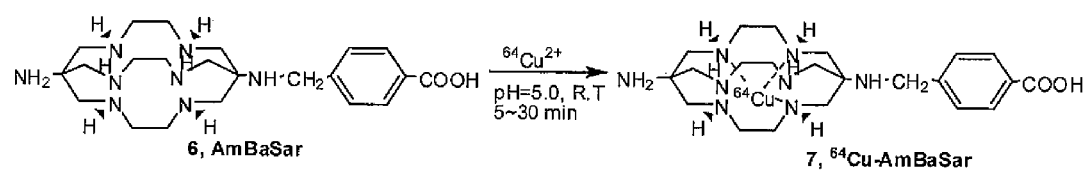
FIG. 9 is a chart depicting a method for the radiosynthesis of $^{64}$Cu-AmBaSar.

FIG. 9 shows a method for the $^{64}$Cu radiolabeling of AmBaSar according to the present invention. AmBaSar (2.5~25 μg) was labeled with $^{64}$Cu (1~5 mCi) in 0.1 M ammonium acetate solution (pH 5.0) at room temperature (23~25° C.) for 5 min to 30 min. After 5 min complexation, the radiolabeling yield of $^{64}$Cu-AmBaSar was more than 97%. The AmBaSar was nearly quantitatively labeled with $^{64}$Cu$^{2+}$ within 30 min under the above experimental conditions. The complexation rates by the AmBaSar at pH 5 with $^{64}$Cu$^{2+}$ was satisfactory for its use in the development of $^{64}$Cu-radiopharmaceuticals. In conclusion, the new functionalized AmBaSar can efficiently label $^{64}$Cu$^{2+}$ at room temperature due to the provision of a three-dimensional hexa-aza cage by increasing thermodynamic and kinetic stability to the $^{64}$Cu$^{2+}$ complex, which is similar with other Sar based ligands.

Figure 10:
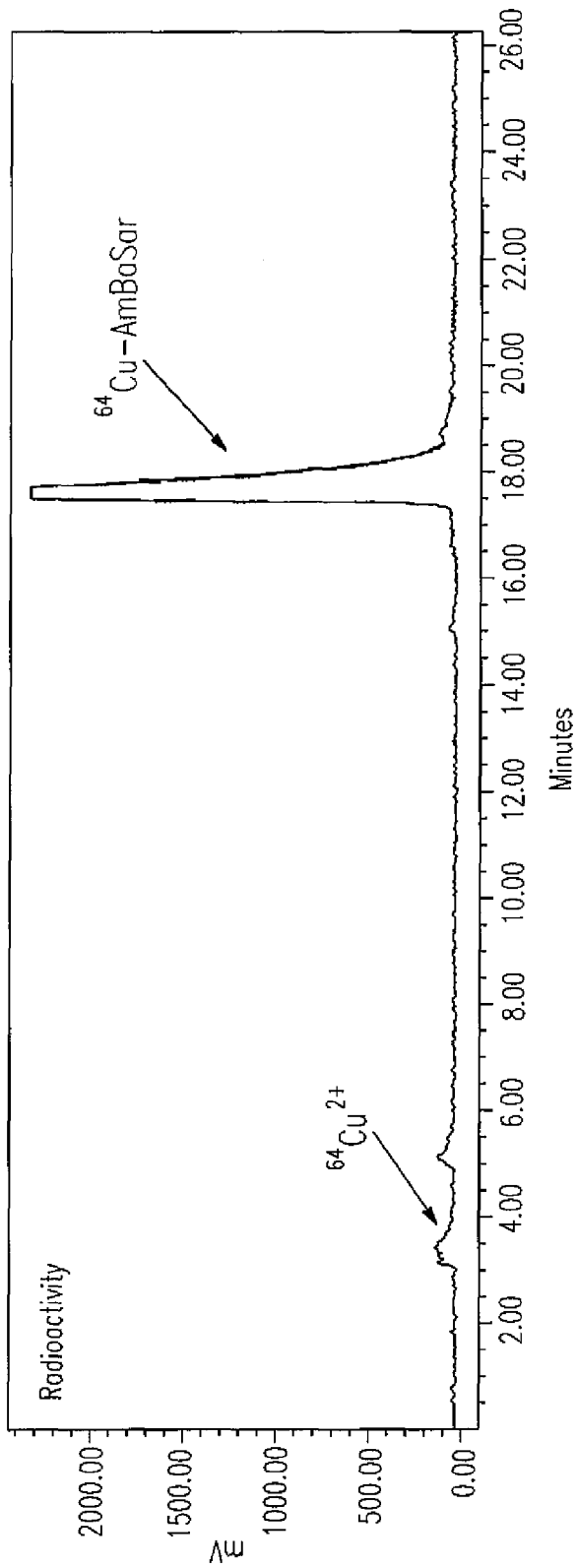
FIG. 10 is a representative chromatogram of crude $^{64}$Cu-AmBaSar using analytical HPLC system

The radiochemical yield of $^{64}$Cu-AmBaSar was determined by radio-HPLC or radio-TLC after different time points. In HPLC, the free $^{64}$Cu was eluted at about 3.6 min, while the retention time of $^{64}$Cu-AmBaSar was 17.9 min. A typical HPLC of crude $^{64}$Cu-AmBaSar is shown in FIG. 10. For TLC, the $R_f$ value of free $^{64}$Cu and complexed $^{64}$Cu-AmBaSar were well-separated. $^{64}$Cu remained at the origin ($R_f$=0) and the $^{64}$Cu-AmBaSar complex close to solvent front ($R_f$=0.71). The radiochemical yield of $^{64}$Cu-AmBaSar was determined to be more than 98%.

$^{64}$Cu-DOTA was prepared following literature procedures. (Refs. 25, 26) The radiochemical yield of $^{64}$Cu-DOTA was determined by radio-TLC after different time points. The radiochemical yield of $^{64}$Cu-DOTA was more than 98% after the complexation.

Lipophilicity (Octanol/Water Partition Coefficient) Studies.

Information about the lipophilicity of the $^{64}$Cu-AmBaSar and $^{64}$Cu-DOTA was obtained by measuring their partitioning in a 1-octanol/water system. Counts in samples were used to determine partition coefficients (log P) values, calculated using a known formula. The log P values were measured at pH 7.4 in PBS. The log P value of $^{64}$Cu-AmBaSar is −2.6, and the corresponding value of $^{64}$Cu-DOTA is −2.3. Both $^{64}$Cu-AmBaSar and $^{64}$Cu-DOTA are hydrophilic. This indicates that they should be predestined to show rapid blood clearance and preferential renal excretion.

In Vitro Studies.

Figure 11:
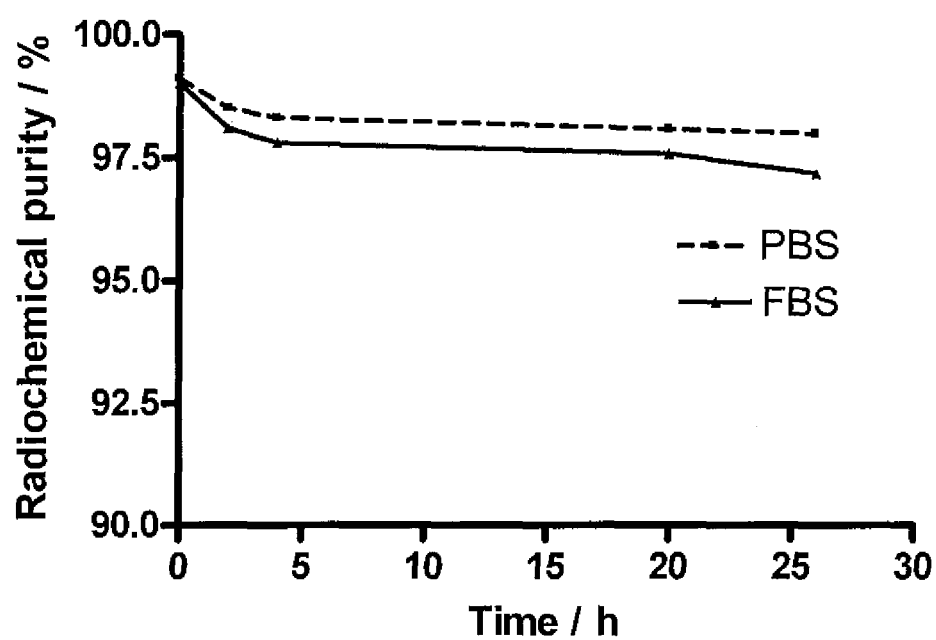
FIG. 11 is a graph showing the in vitro stability of $^{64}$Cu-AmBaSar in PBS (pH 7.4) and FBS at 37° C.

The stability of the BFC copper-64 complex under physiological conditions is very important. In vitro stability of $^{64}$Cu-AmBaSar in PBS (pH 7.4) and FBS solutions at physiological temperatures was tested and the results are shown in FIG. 11. In vitro stability of $^{64}$Cu-AmBaSar was determined in the PBS or FBS using HPLC or TLC after incubating for different time intervals (2, 4, 20, and 26 h). The radiochemical purity of $^{64}$Cu-AmBaSar in the PBS or FBS is more than 97% after 26 hours incubation. The stability of $^{64}$Cu-AmBaSar in mouse blood was also Over 98% of $^{64}$Cu-AmBaSar remained untouched after its incubation for 4 h. These in vitro stability studies demonstrated that the $^{64}$Cu-AmBaSar is very stable in PBS, FBS, and the blood at physiological pH.

In Vivo Studies.

Figure 12:
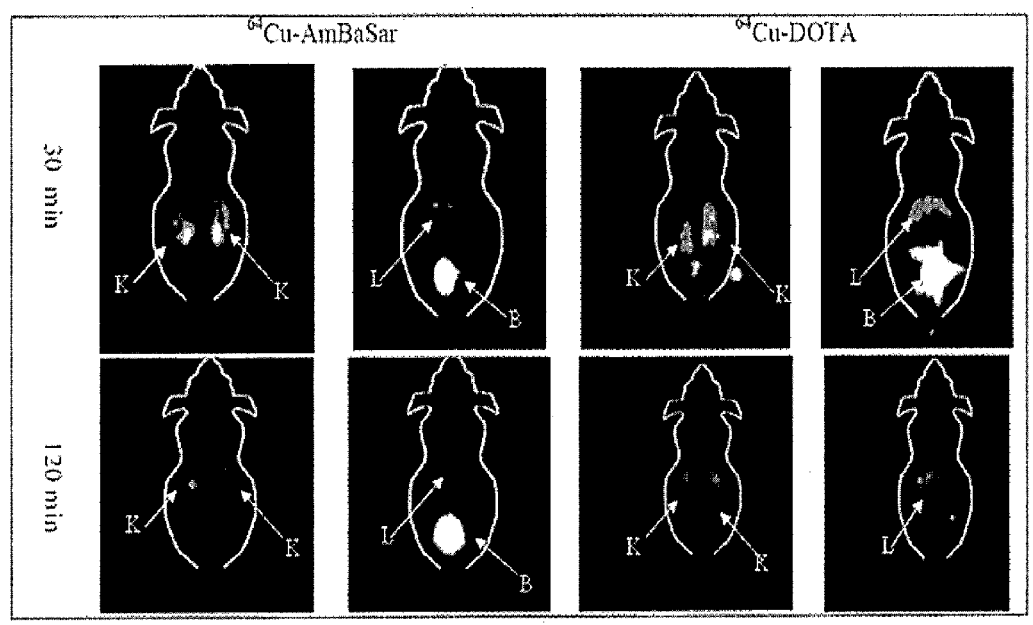
FIG. 12 shows coronal sections of a microPET study of Balb/c mouse after single intravenous of $^{64}$Cu-AmBaSar and $^{64}$Cu-DOTA at 30 min and 2 hour. K=Kidney; L=Liver; B=Bladder.

MicroPET imaging and biodistribution studies were performed with the non-targeted $^{64}$Cu-AmBaSar and $^{64}$Cu-DOTA complexes to allow a comparison of their base-line organ uptake and clearance properties. The micro-PET imaging results were shown in FIG. 12. After 30 min, the radioactivity quickly cleared from muscle and blood, and mainly localized in the bladder and kidneys. Regarding $^{64}$Cu-DOTA, the radioactivity mainly localized in the bladder, kidneys, and liver. At the 30 min time point, both $^{64}$Cu-DOTA and $^{64}$Cu-AmBaSar showed high kidney uptake, with $^{64}$Cu-DOTA having a much higher liver uptake than $^{64}$Cu-AmBaSar. By two hours renal activity cleared significantly for both agents, although liver and bowel activity remained in the animals receiving $^{64}$Cu-DOTA. Although more detailed pharmacokinetic analyses are required, renal activity for $^{64}$Cu-AmBaSar decreased by 51% between 30 min and 2 hours based on the micro-PET region of interest quantification, comparing favorably with $^{64}$Cu-DOTA clearance (66%).

Figure 13:
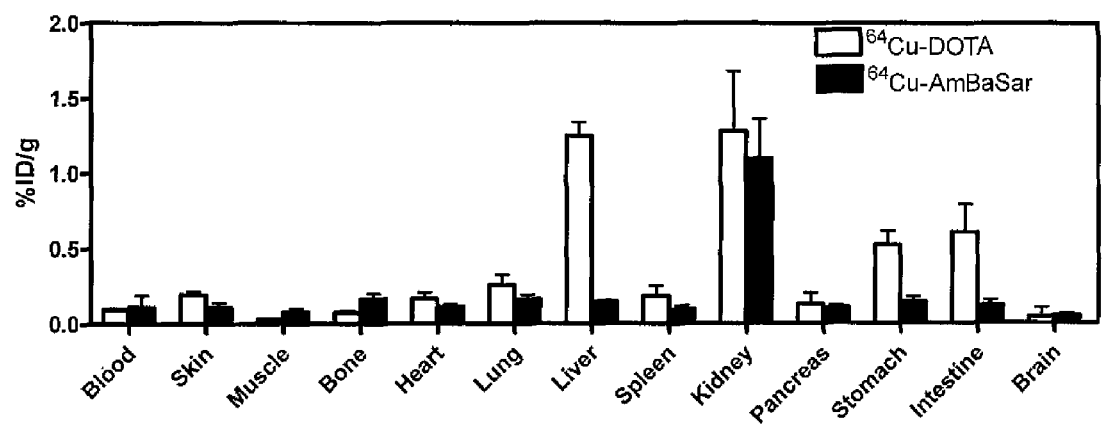
FIG. 13 is a graph showing the biodistribution of $^{64}$Cu-AmBaSar and $^{64}$Cu-DOTA in Balb/C mice after 2 h postinjection.

The biodistribution of $^{64}$Cu-AmBaSar and $^{64}$Cu-DOTA were assessed in Balb/c mice. Each animal was sacrificed at the time interval 2 h and the organs dissected. The values of percent injected dose/gram (ID/g %) in different organs were compared and illustrated in FIG. 13. The $^{64}$Cu-AmBaSar cleared rapidly from the blood and predominantly through the kidneys. After 2 h, the kidney and liver uptake reached 1.09±0.27, 0.14±0.01% ID/g, respectively, which is consistent with the excretion pattern from the microPET imaging results. The $^{64}$Cu-DOTA cleared through the kidney and liver, with uptake reached 1.28±0.41, 1.25±0.09, respectively, by 2 h.

Copper ion in vivo is responsible for many enzymatic processes and hence can be bound by many proteins. Its natural excretory path is via the hepatocytes in the liver. It may be recirculated by binding to ceruloplasmin in the liver. While rapid clearance through the kidneys is typical of charged $^{64}$Cu-complexes which maintain their identity, hepatobiliary clearance of $^{64}$Cu-radiopharmaceuticals is much less desirable, and its presence usually suggests loss of Cu-64 from the ligand. (1, 28) Prasanphanich A F, Retzloff L, Lane S R, Nanda P K, Sieckman G L, Rold T L, et al. In vitro and in vivo analysis of [$^{64}$Cu—NO2A-8-Aoc-BBN(7-14)NH$_2$]: a site-directed radiopharmaceutical for positron-emission tomography imaging of T-47 D human breast cancer tumors. Nucl Med Biol 2009; 36:171-81. Rapid renal clearance, as opposed to mixed renal and hepatic clearance resulting from administration of $^{64}$Cu-DOTA, will provide better somatic contrast from the imaging perspective, and potentially reduce radiation exposure for therapeutic analogues. Therefore, the development of more stable chelators would be beneficial as free Cu clears through liver. The hydrophilicity of $^{64}$Cu-AmBaSar (log P=−2.6) is only slightly different from $^{64}$Cu-DOTA (log P=−2.3). Both compounds should mainly clear through the kidneys. For $^{64}$Cu-AmBaSar, residual kidney uptake and low liver accumulation at 2 h post injection were observed in both the microPET images and biodistribution studies, compared with high residual liver and bowel accumulation with $^{64}$Cu-DOTA. However, with similar hydrophilicity, the liver uptake of $^{64}$Cu-DOTA is eight times higher than that of $^{64}$Cu-AmBaSar. The comparative data from microPET imaging and biodistribution studies between $^{64}$Cu-AmBaSar and $^{64}$Cu-DOTA supports the assumption that $^{64}$Cu-AmBaSar is more stable in vivo than $^{64}$Cu-DOTA. Nonetheless, the differential organ uptake and clearance properties could also be partially attributed to the characteristics of the BFC AmBaSar with polyamine functional groups, and DOTA with polyacid functional groups. Although accumulation of radioactivity in liver is likely related to the loss $^{64}$Cu from the DOTA chelator, further biochemical testing may be required to determine the disposition of $^{64}$Cu in liver.

Materials and Methods

Bifunctional Chelator AmBaSar Labeling Copper-64.

[$^{64}$Cu]Acetate (64 Cu(OAc)$_2$) was prepared by adding 185 MBq (5 mCi) of $^{64}$CuCl$_2$ in 0.1 M HCl into an 1.5 mL microfuge tube containing 300 μL 0.1 M ammonium acetate (pH 5.0). The mixture was vortexed and incubated for 15 min at room temperature. AmBaSar (2.5-25 μg), diluted in 100 μL of 0.1 M ammonium acetate (pH 5.0), was mixed with 1~5 mCi of $^{64}$Cu(OAc)$_2$. The solution was then incubated at room temperature (23~25° C.) for 5 min~30 min. The radiochemical yield was determined by radio-HPLC or radio-TLC at different time points. $^{64}$Cu-AmBaSar was purified by radio-HPLC, and the eluant was evaporated and reconstituted in saline, which was filtered into a sterile dose vial for use in animal experiments by passage through a 0.22 μm Millipore filter.

Bifunctional Chelator DOTA Labeling Copper-64.

DOTA (20 μg) was labeled with $^{64}$Cu$^{2+}$ by addition of 2 mCi of $^{64}$Cu$^{2+}$ in 0.1 M sodium acetate buffer (pH 5.5) followed by 45 min incubation at 45° C. The radiochemical yield was determined by radio-TLC (the same condition with $^{64}$Cu-AmBaSar).

Determination of the Partition Coefficient Log P.

The partition coefficient value was expressed as log P. Log P of $^{64}$Cu-AmBaSar or $^{64}$Cu-DOTA was determined by measuring the distribution of radioactivity in 1-octanol and PBS. A 5 μL sample of $^{64}$Cu-AmBaSar or $^{64}$Cu-DOTA in PBS was added to a vial containing 1 mL each of 1-octanol and PBS. After vortexing for 5 min, the vial was centrifuged for 5 min to ensure complete separation of layers. Then, 5 μL of each layer was pipetted into other test tubes and radioactivity was measured using a gamma counter (Packard). The measurement was repeated three times.

In Vitro Stability Assessment.

The stability of the $^{64}$Cu-AmBaSar was assayed by measuring the radiochemical purity after different incubation times at room temperature or 37° C. For the in vitro stability study, 100 μCi of the $^{64}$Cu-AmBaSar was pipetted into 1 mL of PBS and fetal bovine serum (FBS), respectively, followed by incubation in PBS at room temperature and in FBS at 37° C. An aliquot of the mixture was removed for the determination of radiochemical purity by HPLC at different time points after incubation (2, 4, 20, and 26 h). The solution of FBS was centrifuged, and the upper solution was taken and filtered for HPLC analysis.

MicroPET Imaging and Biodistribution.

MicroPET imaging and biodistribution of the radiolabeled BFCs were performed on Balb/c mice to evaluate their in vivo properties. Animals (Balb/c, n=2) were injected with 0.3 mCi $^{64}$Cu-AmBaSar or $^{64}$Cu-DOTA through the tail vein. PET imaging (10-min static scans) was performed using a microPET R4 scanner (Concorde Microsystems, Inc, Knoxville, Tenn.), with 120 transaxial planes and spatial resolution of 1.2 mm, at 30 min and 2 h postinjection. The microPET data were reconstructed using the ordered subsets expectation maximization (OSEM) algorithm using the microPET Manager Software (CTI Concorde Microsystems, Inc, Knoxville, Tenn.). Images were then analyzed using the Acquisition Sinogram Image Processing (ASIPro) software (CTI Concorde Microsystems, Inc, Knoxville, Tenn.).

For biodistribution studies, one group of mice (Balb/c, n=3) was injected intravenously with the radiotracer $^{64}$Cu-AmBaSar (10 μCi, 100 μL). Another group of mice was injected similarly with $^{64}$Cu-DOTA (10 μCi, 100 μL). Activity injected into each mouse was measured in a dose calibrator (Capintec). After inhalation anesthesia, animals were sacrificed at 2 h postinjection. Tissues and organs of interest were separated and weighed. Radioactivity in each organ was measured using a gamma counter, and radioactivity uptake was expressed as % ID/g. Mean uptake (% ID/g) for each group of animals was calculated with standard deviations.

Copper-64 Labeled AmBaSar Conjugated Cyclic RGD Peptide for Improved MicroPET Imaging of Integrin $\alpha_v\beta_3$ Expression Cu-AmBaSar-RGD was obtained in high yield under mild conditions for PET imaging of integrin $\alpha_v\beta_3$ expression. This tracer exhibits good tumor-targeting efficacy, excellent metabolic stability, as well as favorable in vivo pharmacokinetics. In vitro and in vivo evaluation of the $^{64}$Cu-AmBaSar-RGD shows it has improved in vivo stability compared with the established tracer $^{64}$Cu-DOTA-RGD. The AmBaSar chelator has general application for $^{64}$Cu labeling of various bioactive molecules in high radiochemical yield and high in vivo stability for future PET applications.

Syntheses of AmBaSar-RGD and DOTA-RGD.

AmBaSar could be activated and conjugated to the cyclic RGDyk peptide in a water-soluble procedure as described herein. The conjugation can also be performed in organic phase according to literature procedures (Refs. 29, 30) In brief: the solution of AmBaSar (4.5 mg, 0.01 mmol), HATU (3.8 mg, 0.01 mmol), HOAt (1.4 mg, 0.01 mmol), and dimethyl sulfoxide (DMSO, 0.5 mL) were stirred at room temperature for 10 min. Seven equivalent of DIPEA (9.1 mg, 0.07 mmol) and cyclic RGDyk (1.2 mg, 0.002 mmol) in 300 μL, DMSO were then added to the mixture at 0° C. The mixture was stirred for 3 h at room temperature, and the solvent removed in vacuo. The residue was dissolved in acetonitrile/water (1:3) containing 0.1% TFA and purified by semipreparative HPLC. AmBaSar-RGD was obtained as a white solid material after lyophilization. DOTA was activated and conjugated to cyclic RGDyk according to literature methods. (Ref. 31)

DOTA-RGD was also purified by semipreparative HPLC and confirmed by mass spectrometry. AmBaSar-RGD and DOTA-RGD conjugates were dissolved in 0.1 N ammonium acetate buffer solution (pH 5~5.5), respectively, and stored in −20° C. for the future use in radiolabeling reactions.

Copper-64 Labeling and Formulation.

The $^{64}$Cu-AmBaSar-RGD was prepared as described supra with minor modifications as follows: [$^{64}$Cu]Acetate ($^{64}$Cu (OAc)$_2$) was prepared by adding 37-111 MBq of $^{64}$CuCl$_2$ in 0.1 N HCl into 300 μL 0.1 N ammonium acetate buffer (pH 5.0~5.5), followed by mixing and incubating for 15 min at room temperature. The AmBaSar-RGD (about 2~5 μg in 100 μL 0.1 N ammonium acetate buffer) was added to the above $^{64}$Cu(OAc)$_2$ solution. The resulting mixture was incubated at temperature 23~37° C. for 30 min. The $^{64}$Cu-AmBaSar-RGD was determined and purified by semipreparative HPLC. The radioactive peak containing $^{64}$Cu-AmBaSar-RGD was collected and concentrated by rotary evaporation to remove organic solvent. And the radioactivity was reconstituted in 500-800 μL phosphate buffered saline (PBS), and passed through a 0.22 μm Millipore filter into a sterile dose vial for use in experiments below.

Details of the $^{64}$Cu-labeling DOTA-RGD procedure were reported earlier. (Ref. 31) In brief, 37111 MBq, of $^{64}$CuCl$_2$ in 0.1N HCl were diluted in 300 μL of 0.1 N ammonium acetate buffer pH 5.5), and added to the DOTA-RGD solution (about 2~5 μg in the 100 μL 0.1 N ammonium acetate buffer). The reaction mixture was incubated at 45° C. for 45 min. The radiochemical yield was determined by radio-TLC and HPLC. $^{64}$Cu-DOTA-RGD was then purified by semipreparative HPLC, and the radioactive peak containing the desired product was collected. After removal of the solvent by rotary evaporation, the residue was reconstituted in 500-800 μL of PBS and passed through 0.22 μm Millipore filter into a sterile multidose vial for use in following experiments.

Determination of Log P Value.

The partition coefficient value was expressed as log P. Log P of $^{64}$Cu-AmBaSar-RGD was determined by measuring the distribution of radioactivity in 1-octanol and PBS. A 5 μL sample of $^{64}$Cu-AmBaSar-RGD in PBS was added to a vial containing 1 mL each of 1-octanol and PBS. After vigorously vortexing for 10 min, the vial was centrifuged for 5 min to ensure the complete separation of layers. Then, 3×10 μL of each layer was pipetted into other test tubes and radioactivity was measured using a gamma counter (Perkin-Elmer Packard Cobra). The measurement was repeated three times, and Log P values were calculated according to a known formula.

In Vitro Stability Assay.

The in vitro stability of the $^{64}$Cu-AmBaSar-RGD and $^{64}$Cu-DOTA-RGD were studied at different time points. In brief, 3.7 MBq of the $^{64}$Cu-AmBaSar-RGD and $^{64}$Cu-DOTA-RGD were pipetted into 1 mL of the PBS, fetal bovine serum (FBS), and mouse serum, respectively. After incubated at 37° C. for 3, 18, and 24 h, an aliquot of the mixture was removed from the PBS solution and the radiochemical purity was determined with HPLC. For the solution of FBS and mouse serum, the aliquots were added to 100 μL PBS with 50% TFA. After centrifugation, the upper solution was taken and filtered for HPLC analysis.

Cell Uptake Study.

U87 MG human glioblastoma cell line (integrin $\alpha_v\beta_3$-positive) was obtained from the American Type Culture Collection (ATCC, Manassas, Va.) and maintained under standard conditions according to ATCC as following: The U87 MG glioma cells were grown in Gibco's Dulbecco's medium supplemented with 10% fetal bovine serum (FBS), 100 IU/mL penicillin, and 100 μg/mL streptomycin (Invitrogen Co, Carlsbad, Calif.), at 37° C. in humidified atmosphere containing 5% $CO_2$. The U87 MG glioma cells were grown in culture until sufficient cells were available.

The cell uptake study was performed as described in the literature with some modifications. (Ref. 30) Cells were incubated with $^{64}$Cu-AmBaSar-RGD (37 kBq/well) or $^{64}$Cu-DOTA-RGD at 37° C. for 30 min, 60 min, and 120 min. The blocking experiment was performed by incubating U87 MG cells with $^{64}$Cu-AmBaSar-RGD (37 kBq/well) in the presence of 2 μg RGD. The tumor cells were then washed three times with chilled PBS and harvested by 0.1 N NaOH solution containing 0.5% sodium dodecyl sulfate (SDS). The cell suspensions were collected and measured in the gamma counter.

Animal Model.

Athymic nude mice (about 10-20 weeks old, with a body weight of 25-35 g) were obtained from Harlan (Charles River, Mass.). All animal experiments were performed according to a protocol approved by University of Southern California Institutional Animal Care and Use Committee. The U87 MG human glioma xenograft model was generated by subcutaneous injection of 5×10$^6$ U87 MG human glioma cells into the front flank of athymic nude mice. The tumors were allowed to grow 3-5 weeks until 200-500 mm$^3$ in volume. Tumor growth was followed by caliper measurements of the perpendicular dimensions.

MicroPET Imaging and Blocking Experiment.

MicroPET scans and imaging analysis were performed using a rodent scanner (microPET R4; Siemens Medical Solutions) as previously reported (26). [26] Li, Z., Cai, W., Cao, Q., Chen, K., Wu, Z., He, L., and Chen, X. (2007) $^{64}$Cu-labeled tetrameric and octameric RGD peptides for small-animal PET of tumor $\alpha_v\beta_3$ integrin expression. *J Nucl Med* 48, 1162-71. About 11.1 MBq of $^{64}$Cu-AmBaSar-RGD or $^{64}$Cu-DOTA-RGD was intravenously injected into each mouse under isoflurane anesthesia. Ten minute static scans were acquired at 1, 2, 4, and 20 h post injection. The images were reconstructed by a 2-dimensional ordered-subsets expectation maximum (OSEM) algorithm. For each microPET scan, regions of interest were drawn over the tumor, normal tissue, and major organs on the decay-corrected whole-body coronal images. The radioactivity concentration (accumulation) within the tumor, muscle, liver, and kidneys were obtained from the mean value within the multiple regions of interest and then converted to % ID/g. For the receptor blocking experiment, mice bearing U87 MG tumors were scanned (10 min static) at 2 h time point after the coinjection of 11.1 MBq of $^{64}$Cu-AmBaSar-RGD or $^{64}$Cu-DOTA-RGD with 10 mg/kg c(RGDyK) per mouse.

Biodistribution Studies.

The U87 MG tumor bearing nude mice (n=3) were injected with 0.37 MBq of $^{64}$Cu-AmBaSar-RGD or $^{64}$Cu-DOTA-RGD to evaluate the biodistribution of these tracers. All mice were sacrificed and dissected at 20 h after the injection of the tracers. Blood, U87 MG tumor, major organs, and tissues were collected and weighed wet. The radioactivity in the tissues was measured using the gamma counter. The results were presented as percentage injected dose per gram of tissue (% ID/g). For each mouse, the radioactivity of the tissue samples was calibrated against a known aliquot of the injected activity. Mean uptake (% ID/g) for each group of animals was calculated with standard deviations.

Metabolic Stability.

The metabolic stabilities of $^{64}$Cu-AmBaSar-RGD and $^{64}$Cu-DOTA-RGD were evaluated in an athymic nude mouse bearing a U87 MG tumor. Sixty minutes after intravenous injection of 11.1 MBq of $^{64}$Cu-AmBaSar-RGD or $^{64}$Cu-DOTA-RGD, the mouse was sacrificed and relevant organs were harvested. The blood was collected and immediately centrifuged for 5 min at 13,200 rpm, and the upper serum solution was added to 100 μL PBS solution containing 50% TFA, followed by mixing and centrifugation for 10 min, and the upper solution was then taken out and filtered for HPLC analysis. Liver, kidneys, and tumor were homogenized using a homogenizer, suspended in 1 mL of PBS buffer, and centrifuged for 10 min at 14,000 rpm, respectively. For each sample, after removal of the supernatant, the solution was added to 100 μL PBS solution containing 50% TFA, followed by mixing and centrifugation for 10 min, and the upper solution was then taken and filtered for HPLC analysis. Radioactivity was monitored using a solid-state radiation detector. The eluent was also collected using a fraction collector (1.5 min/fraction) and the radioactivity of each fraction was measured with the γ counter.

Statistical Analysis.

Quantitative data were expressed as mean±SD. Means were compared using One-way ANOVA and student's t-test. P values≤0.05 were considered statistically significant.

Results

Chemistry and Radiolabeling.

The AmBaSar-RGD conjugate was obtained in about 80% yield after HPLC purification for both aqueous and organic phase procedures. The $^{64}$Cu-labeling (n=7) was achieved in more than 95% decay-corrected yield for $^{64}$Cu-AmBaSar-RGD with radiochemical purity of ≥99%, and 80% radiochemical yield for $^{64}$Cu-DOTA-RGD with radiochemical purity≥98%. $^{64}$Cu-AmBaSar-RGD and $^{64}$Cu-DOTA-RGD were analyzed and purified by HPLC. The HPLC retention times of $^{64}$Cu-AmBaSar-RGD and $^{64}$Cu-DOTA-RGD was 26.5 min and 21.5 min, respectively, under the analytical condition. For radio-TLC analysis, the free $^{64}$Cu$^{2+}$ remained at the origin of TLC plate, while the $R_f$ values of $^{64}$Cu-DOTA-RGD and $^{64}$Cu-AmBaSar-RGD were about 0.8~4.0. The specific activity of $^{64}$Cu-DOTA-RGD and $^{64}$Cu-AmBaSar-RGD was estimated to be about 10.1-22.2 GBq/μmol. Both tracers were used immediately after the formulation.

Log P Value and In Vitro Stability.

Figure 15:
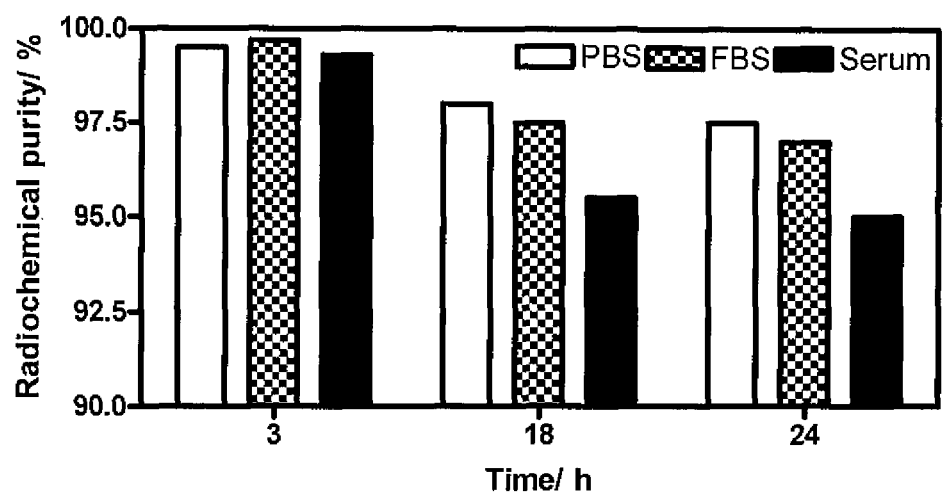
FIG. 15 is a graph showing the in vitro stability of $^{64}$Cu-AmBaSar-RGD in PBS (pH 7.4), FBS, and mouse serum for incubation under 37° C. for 3, 18, and 24 h.

The octanol/water partition coefficients (log P) for $^{64}$Cu-AmBaSar-RGD and $^{64}$Cu-DOTA-RGD were −2.44±0.12 and −2.80±0.04, respectively (Ref. 31), which demonstrated that both tracers are rather hydrophilic. The in vitro stability of $^{64}$Cu-AmBaSar-RGD was also studied in PBS (pH 7.4), FBS, and mouse serum for different time intervals (3, 18, and 24 h) at physiological temperature 37° C. The stability was presented as percentage of intact $^{64}$Cu-AmBaSar-RGD based on the HPLC analysis and the results are shown in FIG. 15. After 24 h incubation, more than 97% of $^{64}$Cu-AmBaSar-RGD remained intact in the PBS and FBS, and more than 95% of $^{64}$Cu-AmBaSar-RGD remained intact in mouse serum. We also found that $^{64}$Cu-DOTA-RGD demonstrated similar stability results in vitro under the above experimental conditions (data not shown).

In Vitro Cell Uptake.

Figure 16:
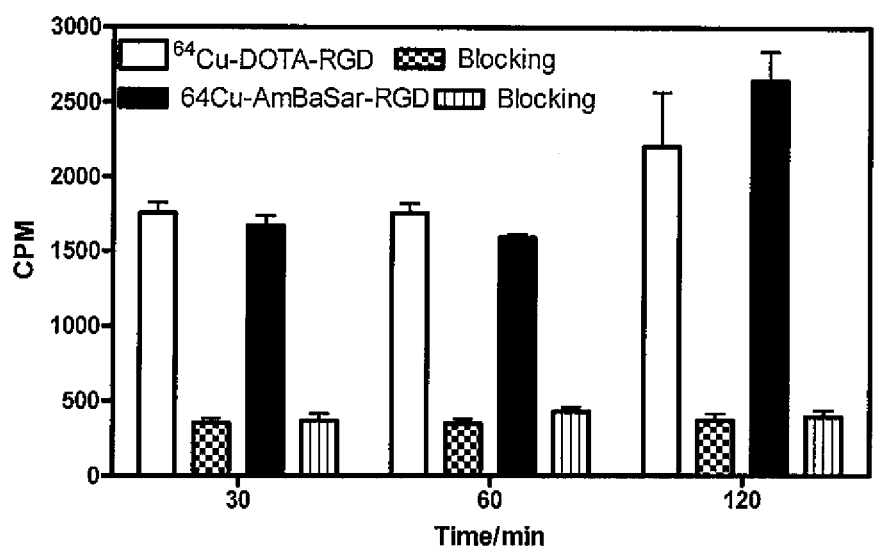
FIG. 16 is a graph showing that the U87 MG cell uptakes of $^{64}$Cu-AmBaSar-RGD and $^{64}$Cu-DOTA-RGD at 0.5, 1, and 2 h in the absence/presence of excess amount of cyclic RGD

Cell uptake study of $^{64}$Cu-AmBaSar-RGD or $^{64}$Cu-DOTA-RGD was performed on U87 MG tumor cells, and the cell uptake was expressed as radioactivity (cpm) per $10^6$ cells after decay correction as shown in FIG. 16. The cell uptake study revealed that both $^{64}$Cu-AmBaSar-RGD and $^{64}$Cu-DOTA-RGD could bind to U87 MG tumor cells, but relatively low amounts of activity (only about 0.1~0.4% was internalized). However, this binding could be efficiently blocked by excess amount of cold cyclic RGD peptide, which demonstrated the binding specificity of the radiolabeled ligands.

MicroPET Imaging.

Figure 17A:
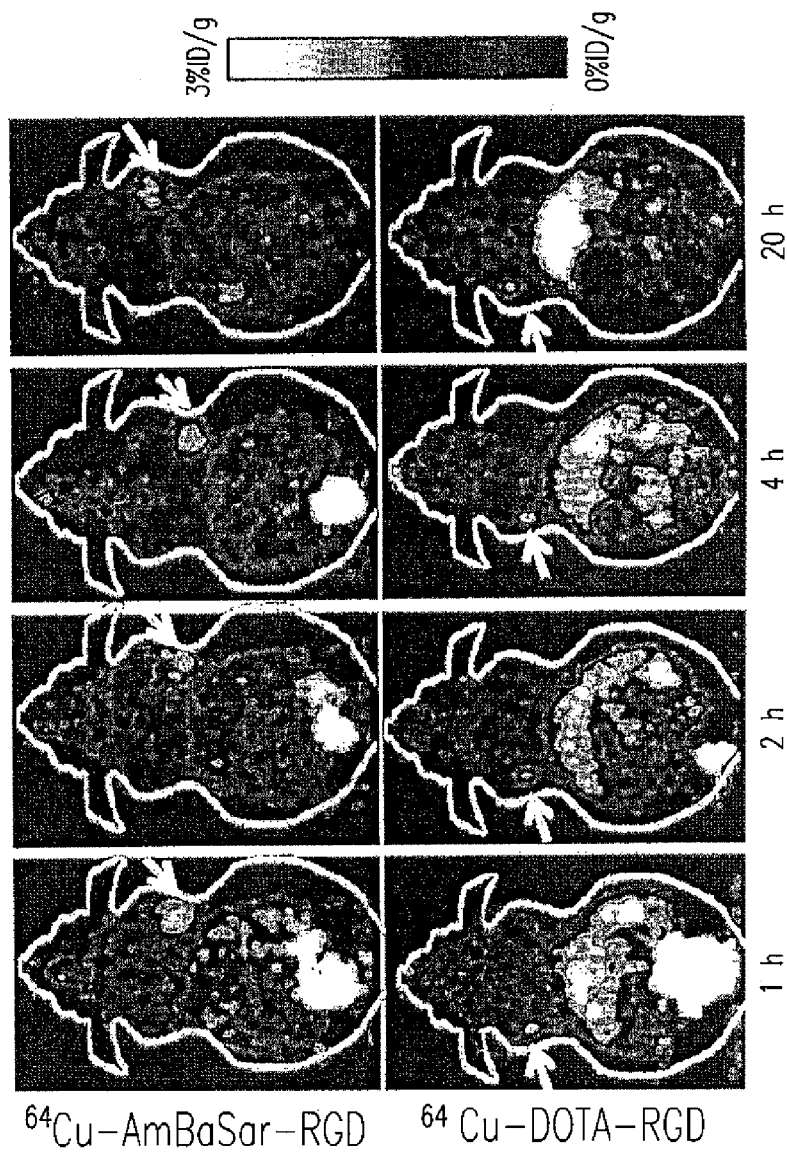
FIG. 17 is a MicroPET study of U87 MG tumor-bearing mice showing: (A) The coronal images of nude mice bearing U87 MG tumor at 1, 2, 4, and 20 h p.i. of $^{64}$Cu-AmBaSar-RGD and $^{64}$Cu-DOTA-RGD; and (B) Time activity curves of $^{64}$Cu-AmBaSar-RGD and $^{64}$Cu-DOTA-RGD in U87 MG tumor, liver, and kidneys (n=3). Tumors are indicated by arrows.
Figure 17B:
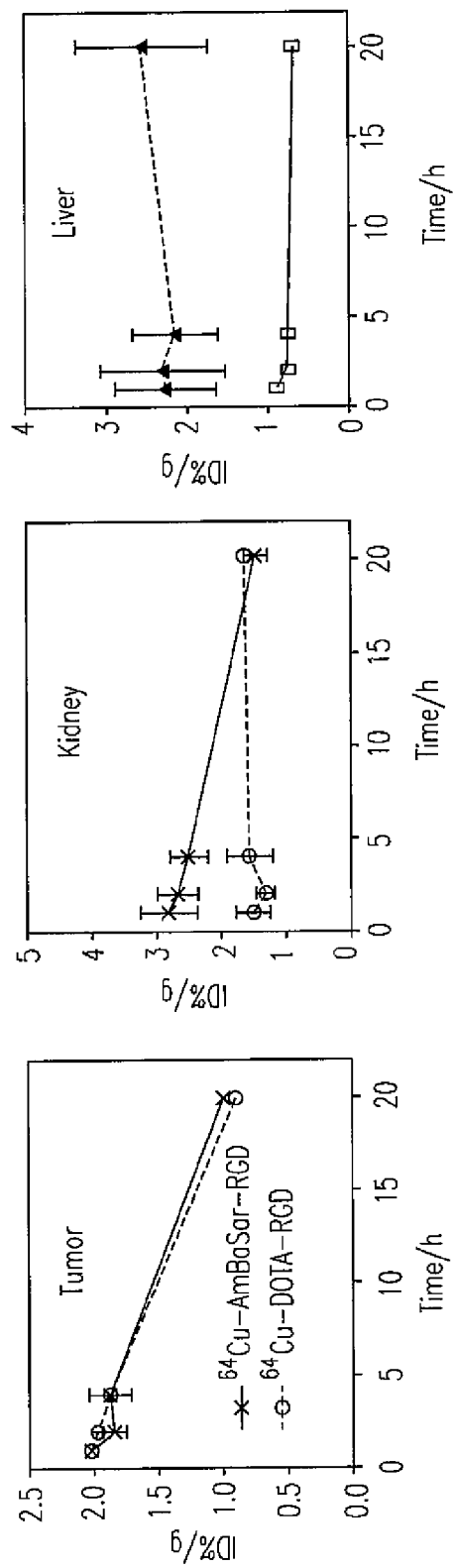

The tumor-targeting efficacy and biodistribution patterns of $^{64}$Cu-AmBaSar-RGD and $^{64}$Cu-DOTA-RGD were evaluated in nude mice bearing U87 MG human glioma xenograft tumors (n=3) at multiple time points (1, 2, 4, and 20 h) with static microPET scans. Representative decay-corrected coronal images at different time points were shown in FIG. 17A. The U87 MG tumors were clearly visualized with high tumor-to-background contrast for both tracers. The uptake of $^{64}$Cu-AmBaSar-RGD in U87 MG tumors was 2.04±0.14, 1.85±0.16, 1.87±0.11, and 0.97±0.05% ID/g at 1, 2, 4, and 20 h p.i., respectively. $^{64}$Cu-DOTA-RGD demonstrated similar tumor uptake with the value of 2.03±0.10, 1.97±0.05, 1.88±0.29, and 0.88±0.07% ID/g at the above time points, respectively (FIG. 4B-3). However, the biodistribution patterns of $^{64}$Cu-AmBaSar-RGD and $^{64}$Cu-DOTA-RGD were significantly different, especially in the kidneys and liver. The renal uptake of $^{64}$Cu-AmBaSar-RGD were 2.83±0.77, 2.68±0.55, 2.49±0.50, and 1.43±0.35% ID/g at 1, 2, 4, and 20 h p.i., respectively; while the corresponding uptake for $^{64}$Cu-DOTA-RGD was 1.52±0.46, 1.33±0.23, 1.55±0.61, and 1.58±0.13% ID/g, respectively. This was lower than that of $^{64}$Cu-AmBaSar-RGD from 1 to 4 h, and reached comparable levels at 20 h time point. The liver uptake for $^{64}$Cu-AmBaSar-RGD was 0.89±0.13, 0.76±0.13, 0.75±0.14, and 0.64±0.06% ID/g at 1, 2, 4, and 20 h p.i. The corresponding uptake value for $^{64}$Cu-DOTA-RGD was 2.28±1.08, 2.31±1.34, 2.15±0.90, and 2.52±1.43% ID/g respectively, which were significantly higher than those of $^{64}$Cu-AmBaSar-RGD at all time points.

Blocking Experiment.

Figure 18:
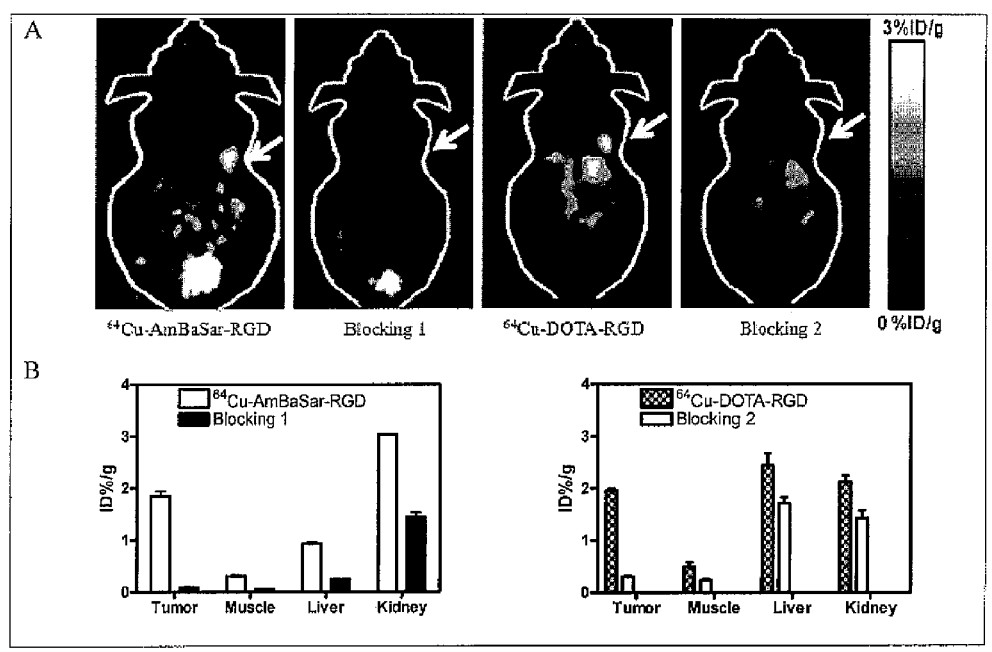
FIG. 18 is a MicroPET imaging study of $^{64}$Cu-AmBaSar-RGD and $^{64}$Cu-DOTA-RGD on U87 MG xenograft mouse model at 2 h p.i. with/without a blocking dose of cyclic RGD: (A) microPET coronal images; (B). Quantitative analyses of microPET imaging of U87 MG tumor, muscle, liver, and kidneys (n=3). Arrows indicate the tumor positions.

The integrin $α_vβ_3$ receptor specificity of $^{64}$Cu-AmBaSar-RGD was confirmed by a blocking experiment where the tracers were co-injected with c(RGDyK) (10 mg/kg). As can be seen from FIG. 18, the U87 MG tumor uptake in the presence of non-radiolabeled RGD peptide (0.09±0.03% ID/g) is significantly lower than that without RGD blocking (1.85±0.16% ID/g) (P≤0.05) at 2 h p.i. The uptake of $^{64}$Cu-AmBaSar-RGD in other organs (heart, intestine, kidneys, lungs, liver, and spleen) was also significantly decreased, which correlates well with previous references. (Ref. 31) Similarly, the integrin $α_vβ_3$ specificity of $^{64}$Cu-DOTA-RGD was confirmed by blocking experiments (FIG. 18).

Biodistribution Studies.

Figure 19B:
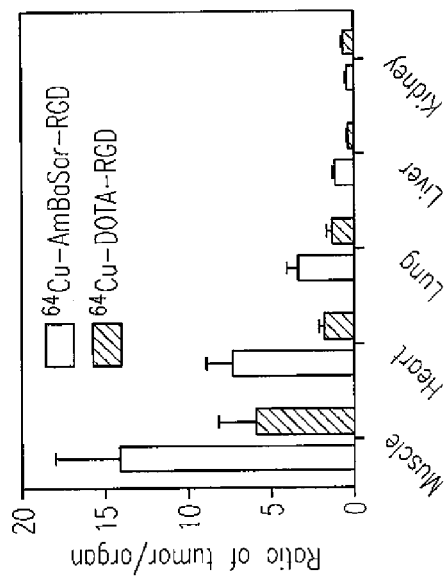
FIG. 19 shows (A) a graph showing biodistribution data for $^{64}$Cu-AmBaSar-RGD and $^{64}$Cu-DOTA-RGD in mice bearing U87 MG glioma xenografts (mean±SD, n=3) at 20 h p.i.; and (B) a graph showing the ratios of tumor to main organs uptake of $^{64}$Cu-AmBaSar-RGD and $^{64}$Cu-DOTA-RGD.
Figure 19A:
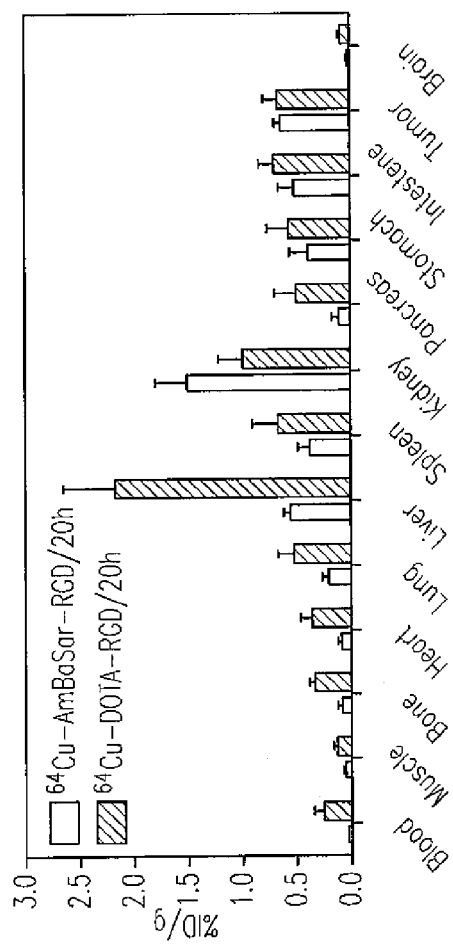

To validate the accuracy of small animal PET quantification, we also performed a biodistribution experiment by using the direct tissue sampling technique. The data shown as the percentage administered activity (injected dose) per gram of tissue (% ID/g) in FIG. 19A. Both $^{64}$Cu-AmBaSar-RGD and $^{64}$Cu-DOTA-RGD mainly accumulated in kidneys, liver, stomach, intestine, and tumor. After 20 h p.i., the kidneys and liver uptake reached 1.51±0.27 and 0.55±0.06% ID/g for $^{64}$Cu-AmBaSar-RGD, and 0.98±0.40 and 2.16±0.85% ID/g for $^{64}$Cu-DOTA-RGD, respectively. This difference was consistent with the excretion pattern from the microPET imaging results. Based on the biodistribution results, we also calculated the contrast of tumor to main organs, which is shown in FIG. 19B. For $^{64}$Cu-AmBaSar-RGD, the ratio of tumor uptake to muscle, heart, lung, liver, and kidney uptake was 14.20±3.84, 7.33±1.55, 3.34±0.70, 1.18±0.05, and 0.43±0.06, respectively; while the corresponding value for $^{64}$Cu-DOTA-RGD were 5.97±2.25, 1.78±0.37, 1.27±0.37, 0.33±0.09, and 0.66±0.04, respectively.

Metabolic Stability of $^{64}$Cu-AmBaSar-RGD and $^{64}$Cu-DOTA-RGD.

Figure 20A:
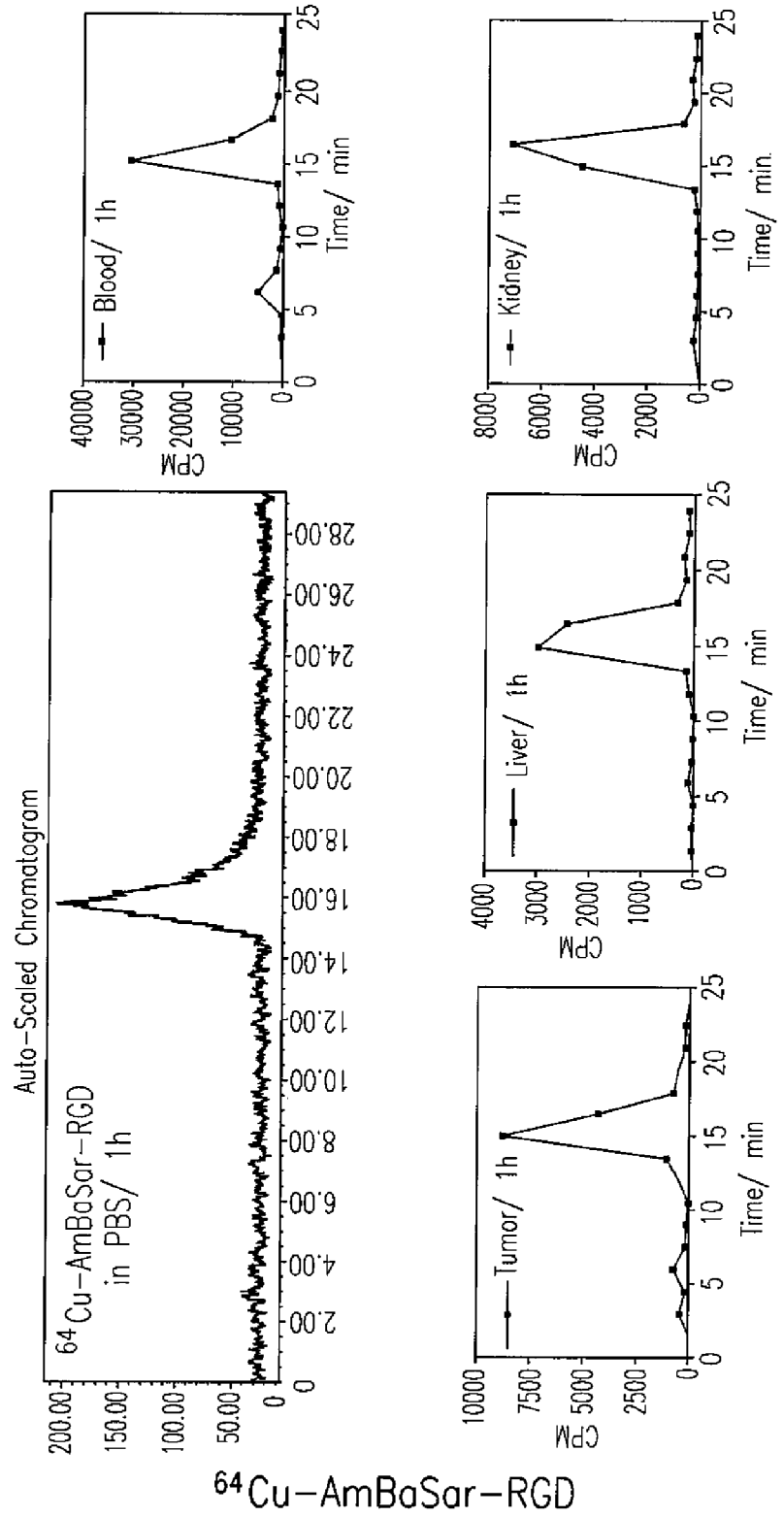
FIG. 20 Metabolic stability of $^{64}$Cu-AmBaSar-RGD (A) and $^{64}$Cu-DOTA-RGD (B) in mouse blood sample and in liver, kidney and U87MG tumor homogenates at 1 h post injection. The HPLC profiles of pure $^{64}$Cu-AmBaSar-RGD (A) and $^{64}$Cu-DOTA-RGD (B) (Standard) are also shown.
Figure 20B:
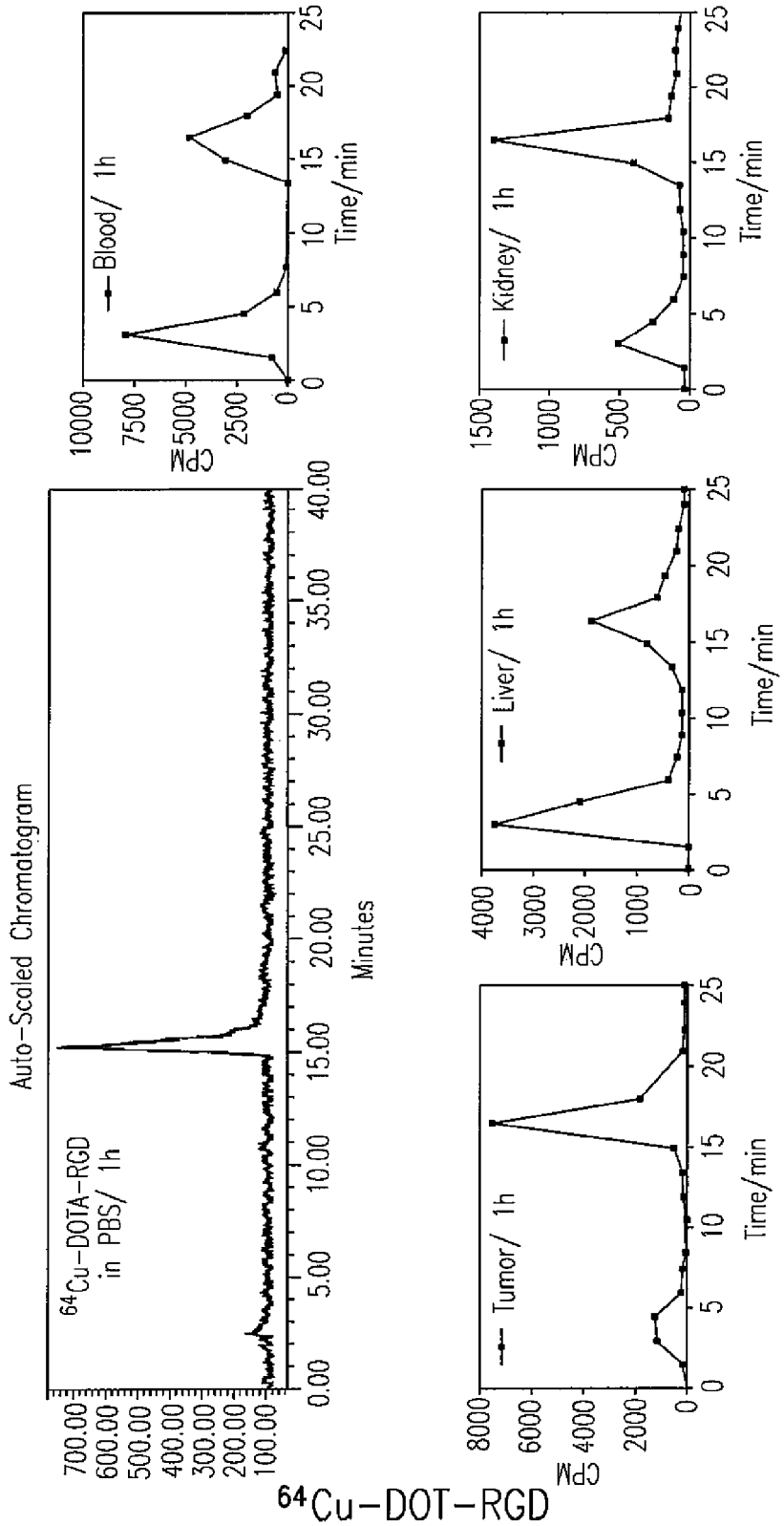

The metabolic stability of $^{64}$Cu-AmBaSar-RGD and $^{64}$Cu-DOTA-RGD were determined in mouse blood and in liver, kidney and tumor homogenates at 1 h after intravenous injection of radiotracer into a U87MG tumor-bearing mouse according to the literature procedures. (Refs. 32, 33). The radioactivity of each sample was analyzed by HPLC and the representative radio-HPLC profiles were shown in FIG. 20. The retention time of free $^{64}$Cu$^{2+}$ was around 3.0 min and the $^{64}$Cu-AmBaSar-RGD complex was around 15~46 min (FIG. 20A). The amount of intact tracer in the blood, tumor, liver, and kidneys were approximately 88%, 95%, 98%, and 98% for $^{64}$Cu-AmBaSar-RGD (FIG. 20A) and 38%, 87%, 34%, and 74% for $^{64}$Cu-DOTA-RGD (FIG. 20B) at 1 h post injection, respectively.

These experiments demonstrated the $^{64}$Cu-complexing moiety, AmBaSar is a superior ligand for an imaging application and targeted radiotherapy due to its improved stability compared with DOTA. The new PET tracer $^{64}$Cu-AmBaSar-RGD can be used for imaging integrin $α_vβ_3$ expression. Our studies demonstrate that $^{64}$Cu-AmBaSar-RGD and $^{64}$Cu-DOTA-RGD have comparable in vitro stability, lipophilicity, and tumor uptake. However, $^{64}$Cu-AmBaSar-RGD did demonstrate improved in vivo stability and biodistribution pattern compared with $^{64}$Cu-DOTA-RGD.

For radiochemistry, the $^{64}$Cu$^{2+}$ labeling condition of AmBaSar-RGD was more favorable and the $^{64}$Cu-AmBaSar-RGD could be obtained with higher radiochemical yield (≥95%) and purity (≥99%) under mild conditions (pH 5.0~5.5, 23~37° C.) in less than 30 min, compared with 90% radiochemical yield for $^{64}$Cu-DOTA-RGD after incubation at 45° C. for 45 min.

Under in vitro conditions, both $^{64}$Cu-AmBaSar-RGD and $^{64}$Cu-DOTA-RGD were very stable in PBS, FBS, and mouse serum solutions at physiological temperature. The Log P is a very useful parameter that can be used to understand the behavior of drug molecules and predict the distribution of a drug compound in a biological system in combination with the other parameters. (Ref. 34). The 10 g P values of $^{64}$Cu-AmBaSar-RGD and $^{64}$Cu-DOTA-RGD indicated that both tracers are rather hydrophilic and they should show rapid blood clearance and preferential renal excretion if they are stable in vivo. However, compared with $^{64}$Cu-AmBaSar-RGD, $^{64}$Cu-DOTA-RGD had significantly higher liver uptake (~2-3 times) based on microPET imaging and biodistrbution studies, which indicated that $^{64}$Cu-DOTA-RGD is less stable than $^{64}$Cu-AmBaSar-RGD in vivo. In microPET studies, the U87 MG tumor uptake of $^{64}$Cu-AmBaSar-RGD and $^{64}$Cu-DOTA-RGD were comparable at selected time points, and the binding specificity was proven by the blocking experiment. The biodistribution study was consistent with the microPET studies. Similar tumor uptake of both tracers may be attributed to their comparable hydrophilicity and the minimal impact of chelators on the integrin binding affinity of RGD peptides. (Ref. 35) $^{64}$Cu-AmBaSar-RGD cleared rapidly from the blood and predominantly through the kidneys and $^{64}$Cu-DOTA-RGD mainly cleared through both kidneys and liver. This difference might because that $^{64}$Cu-AmBaSar-RGD is more stable in vivo compared with $^{64}$Cu-DOTA-RGD, which would result in reduced nonspecific binding. To further confirm this statement, we also studied the metabolic stability of $^{64}$Cu-AmBaSar-RGD and $^{64}$Cu-DOTA-RGD in blood, liver, kidneys, and tumor in nude mice bearing U87 MG glioma xenografts after 1 h p.i. injection. Our study clearly demonstrated that the amount of intact $^{64}$Cu-AmBaSar-RGD was much higher than that of $^{64}$Cu-DOTA-RGD in blood, tumor, liver, and kidneys. To the best of our knowledge, this is the first study that directly demonstrates that Sar-type chelator, such as AmBaSar, forms more a stable Cu complex in vivo than the established chelator DOTA through direct comparison of their metabolic stability. The rapid renal clearance of $^{64}$Cu-AmBaSar-RGD, as opposed to the mixed renal and hepatic clearance of $^{64}$Cu-DOTA-RGD, is preferred as it will provide better somatic contrast from the imaging perspective, and potentially reduce radiation exposure.

Although the invention has been described and explained in terms of specific embodiments and especially embodiments related to the specific BFC AmBaSar, it should be understood that the present invention is not limited to the embodiments specifically discussed and the specific embodiments discussed herein are simply illustrative. As will be appreciated by those skilled in the art, the data and information gleaned from the embodiments discussed with respect to AmBaSar are applicable to the disclosed BFCs not specifically discussed throughout the application.

The following references are incorporated herein by reference in their entirety.

REFERENCES

1. Wadas T J, Wong E H, Weisman G R, and Anderson C J. Copper chelation chemistry and its role in copper radiopharmaceuticals. *Curr Pharm Des* 2007; 13:3-16.
2. Smith S V. Molecular imaging with copper-64. *J Inorg Biochem* 2004; 98:1874-901.
3. Liu S. Bifunctional coupling agents for radiolabeling of biomolecules and target-specific delivery of metallic radionuclides. *Adv Drug Deliv Rev* 2008; 60:1347-70.)
4. Ferreira C L, Yapp D T, Lamsa E, Gleave M, Bensimon C, Jurek P, et al. Evaluation of novel bifunctional chelates for the development of Cu-64-based radiopharmaceuticals. *Nucl Med Biol* 2008; 35:875-82.)
5. Tanaka, K., and Fukase, K. (2008) PET (positron emission tomography) imaging of biomolecules using metal-DOTA complexes: a new collaborative challenge by chemists, biologists, and physicians for future diagnostics and exploration of in vivo dynamics. *Org Biomol Chem* 6, 815-28.
6. De Leon-Rodriguez, L. M., and Kovacs, Z. (2008) The synthesis and chelation chemistry of DOTA-peptide conjugates. *Bioconjug Chem* 19, 391-402.)
7. Varner, J. A., and Cheresh, D. A. (1996) Tumor angiogenesis and the role of vascular cell integrin $\alpha_v\beta_3$. *Important Adv Oncol*, 69-87.
8. Wadas, T. J., Deng, H., Sprague, J. E., Zheleznyak, A., Weilbaecher, K. N., and Anderson, C. J. (2009) Targeting the $\alpha_v\beta_3$ integrin for small-animal PET/CT of osteolytic bone metastases. *J Nucl Med* 50, 1873-80.
9. Cai, W., and Chen, X. (2008) Multimodality molecular imaging of tumor angiogenesis. *J Nucl Med* 49 Suppl 2, 113S-28S.
10. Schottelius, M., Laufer, B., Kessler, H., and Wester, H. J. (2009) Ligands for mapping $\alpha_v\beta_3$-integrin expression in vivo. *Acc Chem Res* 42, 969-80.
11. Liu, S. (2006) Radiolabeled multimeric cyclic RGD peptides as integrin $\alpha_v\beta_3$ targeted radiotracers for tumor imaging. *Mol Pharm* 3, 472-87.
12. Gasser G, Tjioe L, Graham iiB, Belousoff M J, Juran S, Walther M, et al. Synthesis, Copper(II) Complexation, $^{64}$Cu-Labeling, and Bioconjugation of a New Bis(2-pyridylmethyl) Derivative of 1,4,7-Triazacyclononane. *Bioconjug Chem* 2008; 19:719-30.
13. N. DiBartolo, A. M. Sargeson, and S. V. Smith, *Org. Biomol. Chem.*, 2006, 4, 3350-3357. K. L. Bennett, S. V. Smith, R. M. Lambrecht, R. J. W. Truscott, and M. M. Sheil, *Bioconjugate Chem.*, 1996, 7, 16-22
14. R. J. Geue, T. W. Hambley, J. M. Harrowfield, and A. M. Sargeson, *J. Am. Chem. Soc.*, 1984, 106, 5478-5488.
15. G. A. Bottomley, I. J. Clark, I. I. Creaser, L. M. Engelhardt, R. J. Geue, K. S. Hagen, J. M. Harrowfield, G. A. Lawrance, P. A. Lay, A. M. Sargeson, A. J. See, B. W. Skelton, A. H. White, and F. R. Wilner, *Aust. J. Chem.*, 1994, 47, 143-179.
16. S. V. Smith, *Q. J. Nucl. Med. Mol. Imaging.*, 2008, 52, 193-202.)
17. S. Burnet, M. H. Choi, P. S. Donnelly, J. M. Harrowfield, I. Ivanova, S. J. Jeong, Y. Kim, M. Mocerino, B. W. Skelton, A. H. White, C. C. Williams, and Z. L. Zeng, *Eur. J. Inorg. Chem.*, 2001, 1869-1881.
18. G. C. Yeh, A. M. Beatty, and J. K. Bashkin, *Inorg. Chem.*, 1996, 35, 3828-3835.
19. A. F. Abdel-Magid, K. G. Carson, B. D. Harris, C. A. Maryanoff, and R. D. Shah, *J. Org. Chem.*, 1996, 61, 3849-3862.
20. N. DiBartolo, A. M. Sargeson, T. M. Donlevy, and S. V. Smith, *J. Chem. Soc., Dalton Trans.*, 2001, 2303-2309
21. M. R. Lewis, J. Y. Kao, A. L. J. Anderson, J. E. Shively, and A. Raubitschek, *Bioconjugate Chem.*, 2001, 12, 320-324.

22. X. Chen, R. Park, M. Tohme, A. H. Shahinian, J. R. Bading, and P. S. Conti, *Bioconjugate Chem.*, 2004, 15, 41-49.
23. T. J. Wadas, and C. J. Anderson, *Nature Protocols*. 2007, 1, 3062-3068.)
24. Yeh G C, Beatty A M, and Bashkin J K. Synthesis and Characterization of Cobalt-Cage Complexes with Pendant Phenol Groups. Inorg Chem 1996; 35:3828-35.
25. Chen X, Hou Y, Tohme M, Park R, Khankaldyyan V, Gonzales-Gomez I, et al. Pegylated Arg-Gly-Asp peptide: $^{64}$Cu labeling and PET imaging of brain tumor $\alpha_v\beta_3$-integrin expression. J Nucl Med 2004; 45:1776-83.
26. Chen X, Park R, Tohme M, Shahinian A H, Bading J R, and Conti P S. MicroPET and autoradiographic imaging of breast cancer alpha v-integrin expression using $^{18}$F- and $^{64}$Cu-labeled RGD peptide. Bioconjug Chem 2004; 15:41-9.)
27. Wadas T J, Wong E H, Weisman G R, and Anderson C J. Copper chelation chemistry and its role in copper radiopharmaceuticals. Curr Pharm Des 2007; 13:3-16.
28. Prasanphanich A F, Retzloff L, Lane S R, Nanda P K, Sieckman G L, Rold T L, et al. In vitro and in vivo analysis of [$^{64}$Cu—NO2A-8-Aoc-BBN(7-14)NH$_2$]: a site-directed radiopharmaceutical for positron-emission tomography imaging of T-47D human breast cancer tumors. Nucl Med Biol 2009; 36:171-81.
29. Achilefu, S., Bloch, S., Markiewicz, M. A., Zhong, T., Ye, Y., Dorshow, R. B., Chance, B., and Liang, K. (2005) Synergistic effects of light-emitting probes and peptides for targeting and monitoring integrin expression. *Proc Natl Acad Sci USA* 102, 7976-81.
30. Decristoforo, C., Hernandez Gonzalez, L, Carlsen, J., Rupprich, M., Huisman, M., Virgolini, I., Wester, H. J., and Haubner, R. (2008) $^{68}$Ga- and $^{111}$Inlabelled DOTA-RGD peptides for imaging of $\alpha_v\beta_3$ integrin expression. *Eur J Nucl Med Mol Imaging* 35, 1507-15.)
31. Chen, X., Park, R., Tohme, M., Shahinian, A. H., Bading, J. R., and Conti, P. S. (2004) MicroPET and autoradiographic imaging of breast cancer $\alpha_v$-integrin expression using $^{18}$F- and $^{64}$Cu-labeled RGD peptide. *Bioconjug Chem* 15, 41-9.
32. Juran, S., Walther, M., Stephan, H., Bergmann, R., Steinbach, J., Kraus, W., Emmerling, F., and Comba, P. (2009) Hexadentate bispidine derivatives as versatile bifunctional chelate agents for copper(II) radioisotopes. *Bioconjug Chem* 20, 347-59.
33. Shi, J., Kim, Y. S., Zhai, S., Liu, Z., Chen, X., and Liu, S. (2009) Improving tumor uptake and pharmacokinetics of $^{64}$Cu-labeled cyclic RGD peptide dimers with Gly$_3$ and PEG$_4$ linkers. *Bioconjug Chem* 20, 750-9).
34. Valko, K. (2004) Application of high-performance liquid chromatography based measurements of lipophilicity to model biological distribution. *J Chromatogr A* 1037, 299-310.
35. Wei, L., Ye, Y., Wadas, T. J., Lewis, J. S., Welch, M. J., Achilefu, S., and Anderson, C. J. (2009) $^{64}$Cu labeled CB-TE2A and diamsar-conjugated RGD peptide analogs for targeting angiogenesis: comparison of their biological activity. *Nucl Med Biol* 36, 277-85.)
36. Smith S V. Sarar technology for the application of Copper-64 in biology and materials science. Q J Nucl. Med Mol Imaging 2008; 52:193-202.
37. Wadas, T. J., Wong, E. H., Weisman, G. R., and Anderson, C. J. (2007) Copper chelation chemistry and its role in copper radiopharmaceuticals. *Curr Pharm Des* 13, 3-16.)
38. Haubner, R., and Wester, H. J. (2004) Radiolabeled tracers for imaging of tumor angiogenesis and evaluation of anti-angiogenic therapies. *Curr Pharm Des* 10, 1439-55.
39. Wei L, Ye Y, Wadas T J, Lewis J S, Welch M J, Achilefu S, et al. $^{64}$Cu-Labeled CB-TE2A and diamsar-conjugated RGD peptide analogs for targeting angiogenesis: comparison of their biological activity. Nucl Med Biol 2009; 36:277-85.

SUMMARY OF SEQUENCES

<110> University of Southern California
Conti, Peter S
Cal, Hancheng
Zibo, Li
<120> Cage-Like Bifunctional Chelators, Copper-64 Radiopharmaceuticals and Pet Imaging Using the Same
<130> 374634-000279
<140> U.S. Ser. No. 12/695,125
<141> 2010Jan. 27
<150> U.S. 61/147,709
<151> 2009Jan. 27
<160> 1
<170> PatentIn version 3.5
<210> 1
<211> 4
<212> PRT
<213> Artificial Sequence
<220>
<223> chemically synthesized peptide
<400> 1
Asp Gly Glu Ala
1

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 1

Asp Gly Glu Ala
1

We claim:

1. A chemical composition comprising:

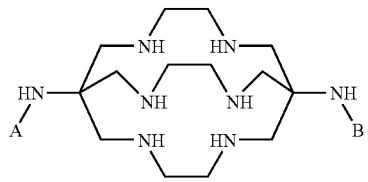

wherein A is a carboxylic acid having the formula:

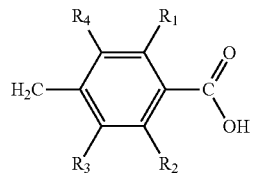

and wherein $R_1$, $R_2$, $R_3$, and $R_4$ are independently selected from the group consisting of H, halogen, alkyl, alkoxy or alkene, and a salt or an ester thereof, and B is a functional group selected from the group consisting of hydrogen, and amine, a carboxylic acid, an ester, a carbonyl, a thiol, an azide and alkene.

2. The chemical composition according to claim 1, wherein $R_1$, $R_2$, $R_3$, and $R_4$ are hydrogen.

3. A chemical composition comprising a molecule selected from the group consisting of:

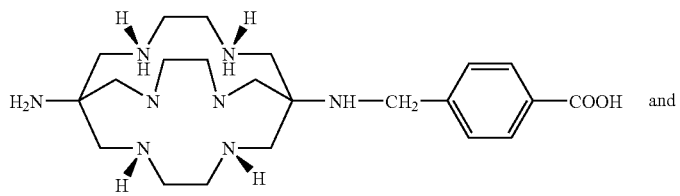

"AmBaSar"

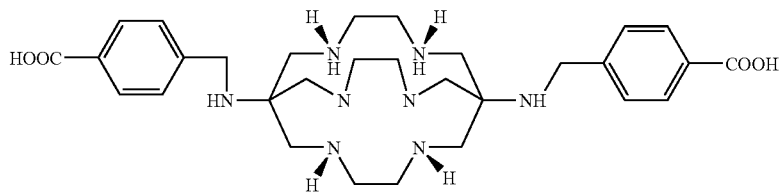

"DiBaSar"

and a salt or an ester thereof.

4. A radiopharmaceutical comprising a compound having the formula:

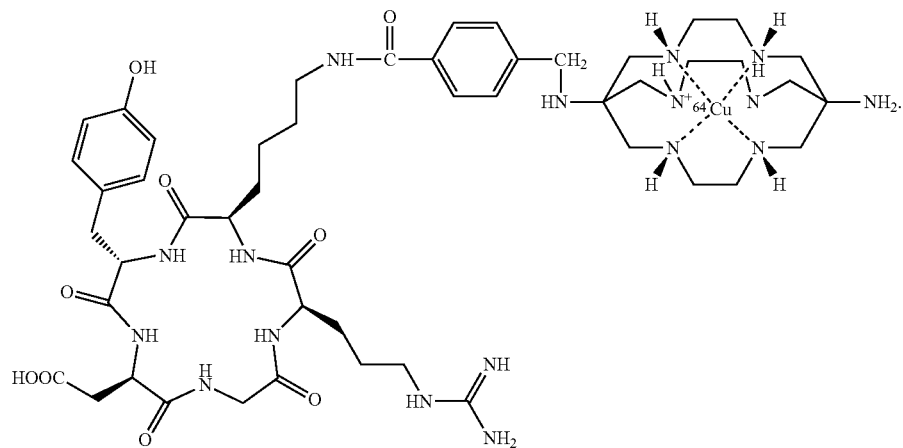

64Cu-AmBaSar-RGD

5. The radiopharmaceutical according to claim 4, further comprising a carrier.

* * * * *

UNITED STATES PATENT AND TRADEMARK OFFICE
CERTIFICATE OF CORRECTION

PATENT NO. : 9,403,875 B2
APPLICATION NO. : 12/695125
DATED : August 2, 2016
INVENTOR(S) : Conti et al.

It is certified that error appears in the above-identified patent and that said Letters Patent is hereby corrected as shown below:

In the Specification

Column 1, Lines 15-17 read:
"This work was supported by research grant from the Department of Energy. The government has certain rights in the invention."
Should read:
--This invention was made with government support under Grant No. DE-SC0002353 awarded by the Department of Energy (DOE). The government has certain rights in the invention.--

Signed and Sealed this
Eighth Day of March, 2022

Drew Hirshfeld
*Performing the Functions and Duties of the
Under Secretary of Commerce for Intellectual Property and
Director of the United States Patent and Trademark Office*